(12) United States Patent
Itoh et al.

(10) Patent No.: US 8,580,991 B2
(45) Date of Patent: Nov. 12, 2013

(54) ALUMINIUM COMPLEXES AND USE THEREOF AS A CATALYST IN INTRAMOLECULAR RING CLOSURE REACTIONS

(75) Inventors: Hisanori Itoh, Hiratsuka (JP); Yoji Hori, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 333 days.

(21) Appl. No.: 13/140,356

(22) PCT Filed: Dec. 17, 2009

(86) PCT No.: PCT/JP2009/071509
§ 371 (c)(1),
(2), (4) Date: Jun. 16, 2011

(87) PCT Pub. No.: WO2010/071227
PCT Pub. Date: Jun. 24, 2010

(65) Prior Publication Data
US 2011/0257412 A1    Oct. 20, 2011

(30) Foreign Application Priority Data
Dec. 17, 2008   (JP) .................................. 2008-321113

(51) Int. Cl.
*C07D 305/00* (2006.01)
*C07F 5/06* (2006.01)

(52) U.S. Cl.
USPC .......................................... 556/172; 549/210

(58) Field of Classification Search
USPC ............ 556/170, 172, 182; 549/210; 568/828
See application file for complete search history.

(56) References Cited

U.S. PATENT DOCUMENTS

| | | | |
|---|---|---|---|
| 6,090,950 A | 7/2000 | Heise | |
| 6,166,260 A | 12/2000 | Heise | |
| 7,550,633 B2 * | 6/2009 | Friedrich et al. | 568/828 |
| 8,329,830 B2 * | 12/2012 | Yang et al. | 525/474 |
| 8,329,931 B2 * | 12/2012 | Itoh et al. | 556/172 |
| 2002/0133046 A1 | 9/2002 | Iwata et al. | |
| 2008/0167504 A1 | 7/2008 | Friedrich et al. | |
| 2008/0207957 A1 | 8/2008 | Friedrich et al. | |
| 2009/0036699 A1 | 2/2009 | Nobis | |
| 2009/0093649 A1 | 4/2009 | Nobis | |
| 2011/0082308 A1 | 4/2011 | Itoh et al. | |

FOREIGN PATENT DOCUMENTS

| | | | | |
|---|---|---|---|---|
| DE | 10 2005 023 953 A1 | 11/2006 | | |
| EP | 1 225 163 A2 | 7/2002 | | |
| EP | 1225163 | * | 7/2002 | .................... 556/172 |
| JP | 2002-212121 A | 7/2002 | | |
| WO | 2006/069659 A1 | 7/2006 | | |
| WO | 2006/092433 A1 | 9/2006 | | |
| WO | 2007/039342 A1 | 4/2007 | | |
| WO | 2009/144906 A1 | 12/2009 | | |

OTHER PUBLICATIONS

Francis Soki, et al., "Homo-vs. heterometallic organoaluminum fencholates: Structures and selectivities", Journal of Organometallic Chemistry, 2008, pp. 2139-2146, vol. 693, No. 12.

Carlos Cativiela, et al., "Asymmetric Synthesis of 2-Aminonorbornane-2-Carboxylic Acids by Diels-Alder Reaction", Tetrahedron Asymmetry, pp. 1295-1304, 1991, vol. 2, No. 12.

Motoichi Indo, "Synthetic flavor", The Chemical Daily Co., Ltd., pp. 106-114, (Mar. 22, 2005).

Dieter Seebach, et al., "TADDOLs, Their Derivatives, and TADDOL Analogues: Versatile Chiral Auxiliaries", Angew. Chem. Int. Ed., 2001, pp. 92-138, vol. 40.

Dieter Seebach, et al., Reduction of Ketones with LiAlH$_4$ Complexes of $\alpha$, $\alpha$, $\alpha^1$, $\alpha^1$-Tetraaryl-1, 3-dioxolane-4, 5-dimethanols (TADDOLs), Croatica Chemica Acta, 1996, pp. 459-484, vol. 69, No. 2.

M. G. Vinogradov, et al., "Organic Chemistry: Asymmetric reduction of ketones with sodium aluminum hydride modified by various chiral diols", Russian Chemical Bulletin, Mar. 2000, pp. 459-464, vol. 49, No. 3.

Teruhiko Ishikawa, et al., "Chiral Lewis Acid-Hydroxylamine Hybrid Reagent for Enantioselective Michael Addition Reaction Directed Towards β-Amino Acids Synthesis", SYNLETT, 1998, pp. 1291-1293.

* cited by examiner

*Primary Examiner* — Noble Jarrell
*Assistant Examiner* — Raymond Covington
(74) *Attorney, Agent, or Firm* — Sughrue Mion, PLLC

(57) ABSTRACT

To provide a process for increasing the proportion of an optical isomer of not only a compound having a closed ring but also a compound not having a closed ring when an optical isomer mixture of a compound having both a formyl group and a double bond capable of causing a carbonyl-ene ring closing reaction in the same molecule is subjected to a ring closing reaction. A process for increasing the proportion of an optical isomer characterized by subjecting an optical isomer mixture of a compound having both a formyl group and a double bond capable of causing a carbonyl-ene ring closing reaction in the same molecule to a ring closing reaction in the presence of a predetermined aluminum complex represented by the general formula: $[Al_2(L^1)_n(L^2)_{3-n}]_m$.

12 Claims, 7 Drawing Sheets

ALUMINIUM COMPLEXES AND USE THEREOF AS A CATALYST IN INTRAMOLECULAR RING CLOSURE REACTIONS

TECHNICAL FIELD

The present invention relates to a process for producing isopulegol and an analogous compound thereof, which are useful as a raw material for a flavor or fragrance etc. and an important precursor for synthesizing menthol. By subjecting an optical isomer mixture of a compound having both a formyl group and a double bond capable of causing a carbonyl-ene ring closing reaction in the same molecule to a ring closing reaction using a novel asymmetric aluminum complex as a catalyst, the present invention can increase the proportion of either d-form or l-form of a compound produced by the ring closing reaction, or the proportion of either d-form or l-form of the optical isomer mixture which is not reacted by ring closure.

In particular, when only one of the optical isomers of citronellal having low enantio selectivity is preferentially reacted, thereby increasing the proportion of the optical isomer, optical resolution of citronellal is successfully made. Alternatively, when a substrate-selective ring closing reaction is conducted, isopulegol having an increased proportion of a predetermined optical isomer which is not reacted by ring closure can be obtained.

BACKGROUND ART

Menthol, particularly, l-menthol, is conventionally a very important flavor or fragrance having a pleasant cooling sensation and is applied to a wide variety of uses. As a process for obtaining l-menthol, a process of optically resolving dl-menthol and an asymmetric synthesis process are known (Synthetic flavor, written by Motoichi Indo, The Chemical Daily Co., Ltd, pp. 106 to 114). In a production step for l-menthol by the asymmetric synthesis, l-isopulegol as a precursor is hydrogenated to obtain l-menthol. In a step of synthesizing the l-isopulegol, a selective ring closing reaction of d-citronellal is important.

As to the selective ring closing reaction of d-citronellal, various processes have long been known. As a highly selective reaction using an aluminum complex as a catalyst, a highly selective ring closing reaction using an aluminum complex having 2,6-diphenylphenoxy moiety as a catalyst has been recently found (Japanese Patent Application Laid-Open No. 2002-212121). Other than this, a ring closing reaction using an aluminum complex having a phenoxy moiety as a catalyst (WO 2006/069659, WO 2006/092433, DE 102005023953) and a ring closing reaction using an aluminum complex having a siloxy moiety as a catalyst (WO 2007/039342) have been reported. However, there are no reports on a selective ring closing reaction of only one of the optical isomers of racemic citronellal by using an optically active aluminum complex. On the other hand, there are many reports on an aluminum catalyst having a biphenol skeleton as an axis-asymmetric ligand and a diol ligand having an asymmetric carbon (U.S. Pat. No. 6,090,950, U.S. Pat. No. 6,166,260, Angew. Chem. Int. Ed, 2001, 40, 92-138, Synlett, 1998, 1291-1293, Tetrahedron: Asymmetry 1991, Vol. 2, No. 12, 1295-1304, CROATIA CHEMICA ACTA, 1996, 69, 459-484 and Russian Chemical Bulletin, 2000, 49, 460-465). However, a catalyst having a ratio of aluminum:biphenol:diol of 2:2:1 or 2:1:2 has not yet been reported.

SUMMARY OF INVENTION

An object of the present invention is to provide a process for obtaining a desired optically active alcohol or optically active olefin aldehyde enhanced in optical purity by causing an intramolecular carbonyl-ene ring closing reaction using a novel asymmetric aluminum complex as a catalyst, thereby increasing the proportion of a predetermined optical isomer of a compound produced by the ring closure or a compound left unreacted, more specifically, to provide a process for obtaining l-isopulegol and l-citronellal or d-isopulegol and d-citronellal by optical resolution of citronellal by a highly selective ring closing reaction.

The present inventors have conducted intensive studies with a view to attaining the above objects. As a result, they found that when a specific catalyst is used, citronellal corresponding to the configuration of an asymmetric ligand can be preferentially ring-closed, with the result that a dl enantio selectivity is improved and further isopulegol is highly selectively (an isomer ratio of 80% or more) obtained from four types of isomers, namely, isopulegol, isoisopulegol, neoisopulegol and neoisoisopulegol, in a high yield. Based on this finding, the present invention has been accomplished.

To be more specific, the present invention encompasses the following inventions.

[1] An aluminum complex represented by the general formula (1') below:

wherein in the formula (1'), n represents an integer of 1 or 2; m represents a natural number; $L^1$ represents a ligand represented by the formula (2') below; $L^2$ represents a ligand represented by the formula (3-A') below or the formula (3-B') below, with the proviso that when n=2, the ligand represented by the formula (2') below is an optically active substance and when n=1, the ligand represented by the formula (3-A') below or the formula (3-B') below is an optically active substance,

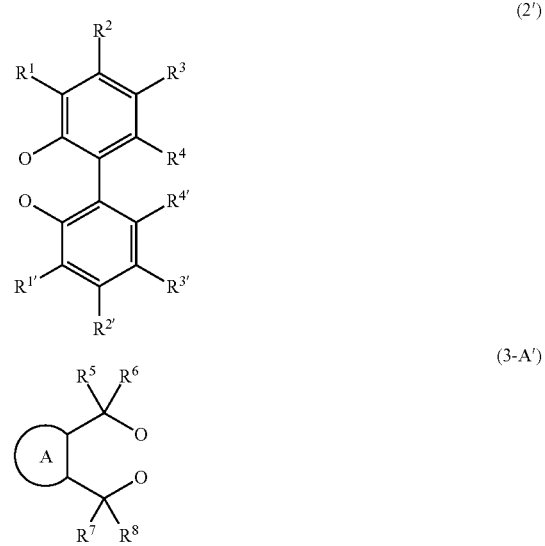

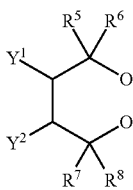
(3-B')

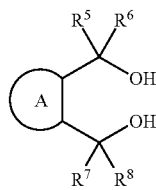
(3-A)

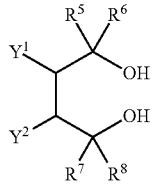
(3-B)

in the formula (2'), $R^1$, $R^2$, $R^3$, $R^4$, $R^{1'}$, $R^{2'}$, $R^{3'}$, and $R^{4'}$ each independently represent a hydrogen atom, a halogen atom, a hydroxy group, a saturated or unsaturated carbon chain, an aryl group that may have a substituent, a heterocyclic group that may have a substituent, an alkoxy group, an aryloxy group, an aralkyloxy group, a carboxy group that may be protected with a protecting group, an amino group, a substituted amino group, a nitro group, an acyl group, a substituted silyl group, a thio group, a mercapto group, or a polymer chain, and $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$, and $R^{2'}$ and $R^{1'}$ may be taken together to form a ring;

in the formula (3-A'), $R^5$, $R^6$, $R^7$, and $R^8$ each independently represent an aryl group that may have a substituent, a heterocyclic group that may have a substituent, an aliphatic chain that may have a substituent or an alicyclic group that may have a substituent, and ring A represents a 3- to 8-membered ring that may have a hetero element, and $R^5$ and $R^6$, and $R^7$ and $R^8$ may be taken together to form a ring; and in the formula (3-B'), $R^5$, $R^6$, $R^7$ and $R^8$ have the same meanings as defined above, $Y^1$ and $Y^2$ each independently represent an aliphatic chain that may have a substituent, an alicyclic group that may have a substituent, an aryl group that may have a substituent, a heterocyclic group that may have a substituent, an alkoxy group, a siloxy group that may have a substituent or a carboxy group, and $R^5$ and $R^6$, and $R^7$ and $R^8$ may be taken together to form a ring.

[2] A process for producing the aluminum complex according to item [1], said process comprising the step of reacting an aluminum compound represented by the general formula (1) below:

$$Al(Lg)_3 \quad (1)$$

wherein in the formula (1), Lg represents an alkyl group, an alkoxy group or a halogen atom,
with a biaryl diol compound represented by the general formula (2) below, and a diol compound represented by the general formula (3-A) below or the general formula (3-B) below:

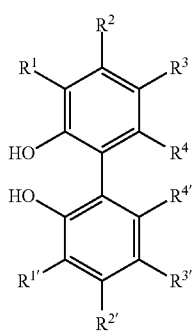
(2)

wherein in the formula (2), $R^1$, $R^2$, $R^3$, $R^4$, $R^{1'}$, $R^{2'}$, $R^{3'}$ and $R^{4'}$ have the same meanings as defined in the formula (2') of item [1];

in the formula (3-A), $R^5$, $R^6$, $R^7$, $R^8$ and ring A have the same meanings as defined in the formula (3-A') of item [1]; and in the formula (3-B), $R^5$, $R^6$, $R^7$, $R^8$, $Y^1$ and $Y^2$ have the same meanings as defined in the formula (3-B') of item [1].

[3] The process for producing the aluminum complex according to item [2], wherein the biaryl diol compound represented by the general formula (2) is an optically active substance.

[4] The process for producing the aluminum complex according to item [2], wherein the diol compound represented by the general formula (3-A) or the general formula (3-B) is an optically active substance.

[5] The process for producing the aluminum complex according to item [2], wherein the biaryl diol compound represented by the general formula (2) is an optically active substance, and the diol compound represented by the general formula (3-A) or the general formula (3-B) is an optically active substance.

[6] A process for producing an optically active compound, said process comprising the step of subjecting an optical isomer mixture of a compound having both a formyl group and a double bond capable of causing a carbonyl-ene ring closing reaction in the same molecule to a ring closing reaction in the presence of the aluminum complex according to item [1], wherein the optically active compound is enriched with either a d-form or l-form compound produced by the ring closing reaction of the compound having both the formyl group and the double bond.

[7] The production process according to item [6], wherein the compound having both the formyl group and the double bond capable of causing the carbonyl-ene ring closing reaction in the same molecule is a compound represented by the general formula (4) below:

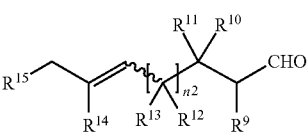
(4)

wherein in the formula (4), n2 represents an integer of 1 or 2; $R^9$, $R^{10}$ and $R^{12}$ each independently represent a hydrogen atom or an alkyl group that may have a substituent; $R^{11}$ represents an alkyl group that may have a substituent or a hydroxy group that may be protected with a protecting group; $R^{13}$, $R^{14}$ and $R^{15}$ each independently represent a hydrogen atom or an alkyl group that may have a substituent; and the wavy line represents an E or Z conformation.

[8] The production process according to item [6], wherein the compound produced by ring closure is a compound represented by the general formula (5) below:

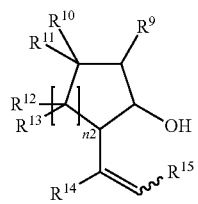
(5)

wherein in the formula (5), n2 represents an integer of 1 or 2; $R^9$, $R^{10}$ and $R^{12}$ each independently represent a hydrogen atom or an alkyl group that may have a substituent; $R^{11}$ represents an alkyl group that may have a substituent or a hydroxy group that may be protected with a protecting group; $R^{13}$, $R^{14}$ and $R^{15}$ each independently represent a hydrogen atom or an alkyl group that may have a substituent; and the wavy line represents an E or Z conformation.

[9] The production process according to item [6], wherein the compound having both the formyl group and the double bond capable of causing the carbonyl-ene ring closing reaction in the same molecule is optically active citronellal and the compound produced by ring closure is optically active isopulegol.

[10] The production process according to item [9], wherein the optically active isopulegol is l-isopulegol.

[11] The production process according to item [9], wherein the optically active citronellal is l-citronellal.

[12] A process for enriching either d-form or l-form in an optical isomer mixture of a compound having both a formyl group and a double bond capable of causing a carbonyl-ene ring closing reaction in the same molecule, said process comprising the step of subjecting the optical isomer mixture to a ring closing reaction in the presence of the aluminum complex according to item [1],
wherein either d-form or l-form is not reacted by ring closure.

According to the present invention, it is possible to obtain a desired optically active alcohol or optically active olefin aldehyde enhanced in optical purity by conducting an intramolecular carbonyl-ene ring closing reaction using a novel aluminum complex as a catalyst, thereby increasing the proportion of a predetermined optical isomer of a compound produced by the ring closure or a compound left unreacted.

DESCRIPTION OF EMBODIMENTS

Figure 1:
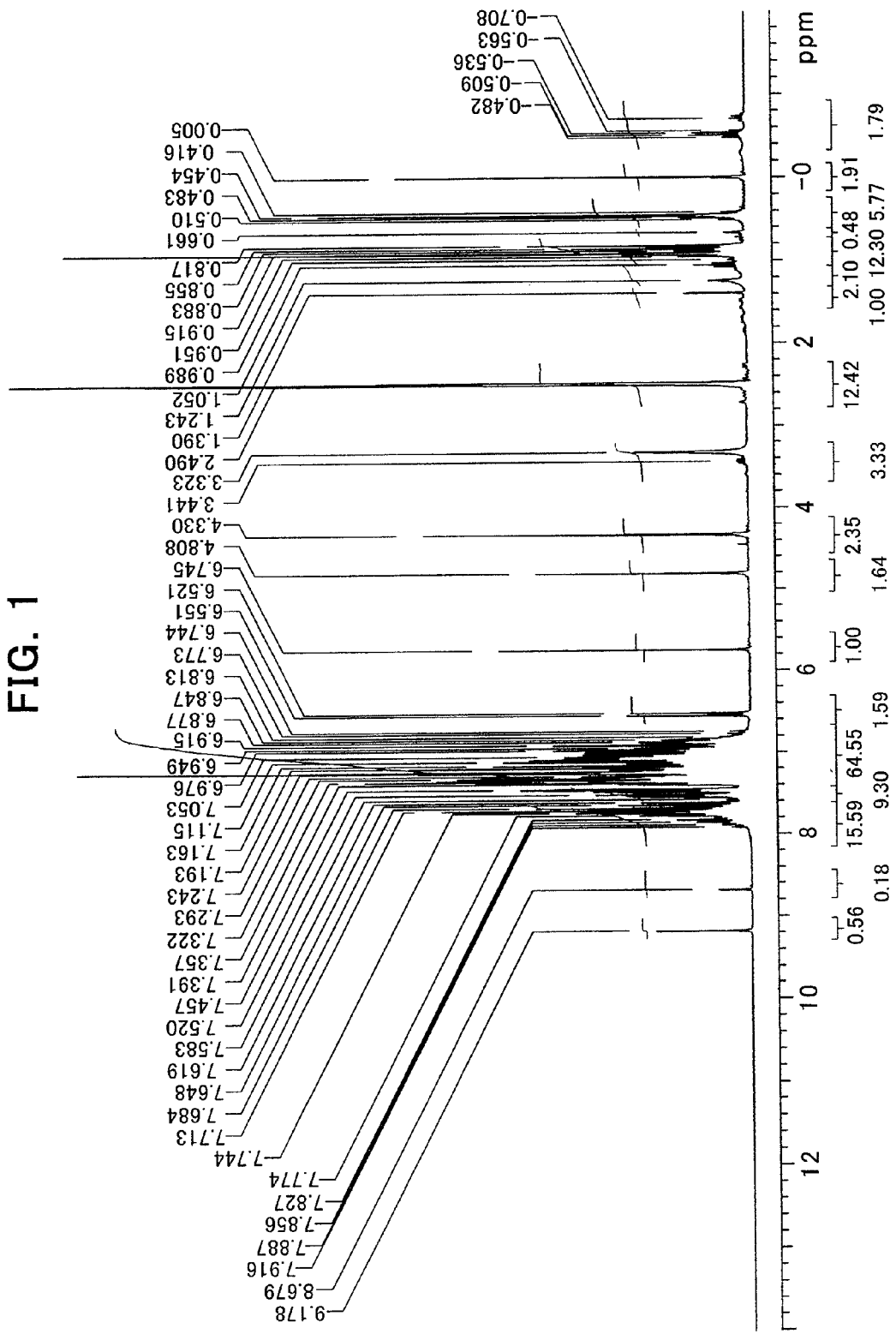
FIG. 1 shows an NMR chart of a solid substance obtained in Example 1.

The present invention will be more specifically described below.

In an aluminum compound represented by general formula (1) to be used for preparing the aluminum catalyst of the present invention, Lg represents an alkyl group, an alkoxy group or a halogen atom.

The alkyl group represented by Lg includes a linear or branched alkyl group having 1 to 8 carbon atoms, preferably 1 to 4 carbon atoms. Specific examples thereof include a methyl group, an ethyl group, a propyl group, an isopropyl group, a n-butyl group, a sec-butyl group, an isobutyl group and a tert-butyl group.

The alkoxy group represented by Lg includes besides an aliphatic alkoxy group, an aryloxy group, an aralkyloxy group and the like. The aliphatic alkoxy group includes a linear or branched alkoxy group having 1 to 8 carbon atoms, preferably 1 to 4 carbon atoms. Specific examples thereof include a methoxy group, an ethoxy group, a propoxy group, an isopropoxy group, a n-butoxy group, a sec-butoxy group, an isobutoxy group, a tert-butoxy group and the like. The aryloxy group includes an aryloxy group having 6 to 14 carbon atoms, preferably 6 to 10 carbon atoms. Specific examples thereof include a phenoxy group, a naphthoxy group and the like. The aralkyloxy group includes a benzyloxy group, a 1-phenethyloxy group and the like.

The halogen atom represented by Lg includes a fluorine atom, a chlorine atom, a bromine atom, an iodine atom and the like.

The groups represented by Lg may be the same or different, and two of three groups may be the same.

Lg is not necessarily an optically active substance.

Preferable examples of an aluminum compound represented by the general formula (1) include trimethylaluminum, triethylaluminum, triisopropylaluminum, tri-n-propylaluminum, tri-n-butylaluminum, triisobutylaluminum, tri-sec-butylaluminum, tri-t-butylaluminum, trimethoxyaluminum, triethoxyaluminum, triisopropoxyaluminum, tri-n-propoxyaluminum, tri-n-butoxyaluminum, tri-sec-butoxyaluminum, tri-t-butoxyaluminum, aluminum trichloride, aluminum tribromide, aluminum triiodide and aluminum trifluoride and the like.

In a diol compound represented by the general formula (2) and a ligand derived from the diol compound and represented by the general formula (2'), $R^1$, $R^2$, $R^3$, $R^4$, $R^{1'}$, $R^{2'}$, $R^{3'}$ and $R^{4'}$ each independently represent a hydrogen atom, a halogen atom, a hydroxy group, a saturated or unsaturated carbon chain, an aryl group that may have a substituent, a heterocyclic group that may have a substituent, an alkoxy group, an aryloxy group, an aralkyloxy group, a carboxy group that may be protected with a protecting group, an amino group, a substituted amino group, a nitro group, an acyl group, a substituted silyl group, a thio group, a mercapto group or a polymer chain. In the general formulas (2) and (2'), $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$ and $R^{2'}$ and $R^{1'}$ may be taken together to form a ring.

In the general formula (1') where n=2, a diol compound represented by the general formula (2) and a ligand derived from the diol compound and represented by the general formula (2') are optically active substances.

In the general formula (1') where n=1, a diol compound represented by the general formula (2) and a ligand derived from the diol compound and represented by the general formula (2') may not be necessarily an optically active substances.

In a biaryl diol compound represented by the general formula (2) and a ligand represented by the general formula (2'), specific examples of the groups represented by $R^1$, $R^2$, $R^3$, $R^4$, $R^{1'}$, $R^{2'}$, $R^{3'}$ and $R^{4'}$ will be described.

The halogen atom includes a fluorine atom, a chlorine atom, a bromine atom, an iodine atom and the like.

The saturated or unsaturated carbon chain includes a linear or branched alkyl group having 1 to 8 carbon atoms such as a methyl group, an ethyl group, a propyl group, an isopropyl group, a n-butyl group, a sec-butyl group, an isobutyl group, a tert-butyl group, a pentyl group and a hexyl group; an alicyclic group having 3 to 14 carbon atoms such as a cyclopentyl group, a cyclohexyl group, a methylcyclohexyl group and a cycloheptyl group; and an alkenyl group and an alkynyl group having 2 to 10 carbon atoms such as an ethynyl group, a vinyl group, a styryl group and an allyl group; and the like.

The aryl group that may have a substituent includes an aryl group having 6 to 14 carbon atoms, preferably 6 to 10 carbon atoms. Specific examples thereof include a phenyl group, a naphthyl group and the like. The substituent that the aryl group has includes an alkyl group having 1 to 4 carbon atoms, an alkoxy group having 1 to 4 carbon atoms and the like.

A heterocyclic group that may have a substituent includes an aliphatic heterocyclic group having 2 to 14 carbon atoms such as a piperidino group, a piperazinyl group, a morpholino group, a tetrahydrofuryl group, a tetrahydropyranyl group and a tetrahydrothienyl group; an aromatic heterocyclic group having 4 to 14 carbon atoms such as a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a chinolyl group, a benzoimidazolyl group, a benzooxazolyl group and a benzothiazolyl group; and the like. The substituent that the heterocyclic group has includes an alkyl group having 1 to 4 carbon atoms and an alkoxy group having 1 to 4 carbon atoms and the like.

The alkoxy group includes an alkoxy group having 1 to 8 carbon atoms, preferably 1 to 4 carbon atoms. Specific examples thereof include a methoxy group, an ethoxy group, a propoxy group, an isopropoxy group, a n-butoxy group, a tert-butoxy group, a pentyloxy group, a hexyloxy group, a heptyloxy group, an octyloxy group and the like.

The aryloxy group includes an aryloxy group having 6 to 14 carbon atoms, preferably 6 to 10 carbon atoms. Specific examples thereof include a phenoxy group, a naphthoxy group and the like.

The aralkyloxy group includes an aralkyloxy group having 7 to 15 carbon atoms, preferably 7 to 11 carbon atoms. Specific examples thereof include a benzyloxy group, a 1-phenethyloxy group and the like.

The carboxy group that may be protected with a protecting group includes a carboxy group; an alkoxycarbonyl group having 2 to 5 carbon atoms such as a methoxycarbonyl group; and the like.

The substituted amino group includes a mono or dialkyl amino group, in which the alkyl group has preferably 1 to 8 carbon atoms, such as an N-methylamino group, an N,N-dimethylamino group, an N,N-diethylamino group, an N,N-diisopropyl amino group or an N-cyclohexyl amino group; a mono or diarylamino group, in which the aryl group has preferably 6 to 14 carbon atoms, such as an N-phenylamino group, an N,N-diphenylamino group, an N,N-ditolylamino group, an N-naphthylamino group or an N-naphthyl-N-phenylamino group; a mono or diaralkylamino group, in which the aralkyl group has preferably 7 to 15 carbon atoms, such as an N-benzylamino group or an N,N-dibenzylamino group; an acylamino group, in which the acyl group has preferably 1 to 8 carbon atoms, such as an acetylamino group, a benzoylamino group or a tert-butoxycarbonylamino group; or the like.

The acyl group includes an aliphatic or aromatic acyl group having 2 to 15 carbon atoms, preferably 2 to 8 carbon atoms. Specific examples thereof include an acetyl group, a propionyl group, a butyryl group, a valeryl group, a pivaloyl group, a benzoyl group, o-, m-, p-toluoyl groups, a p-nitrobenzoyl group and a trifluoroacetyl group.

The substituted silyl group includes a substituted silyl group having 3 to 30 carbon atoms, preferably 3 to 18 carbon atoms. Specific examples thereof include a trimethylsilyl group, a triphenylsilyl group, a tri(p-tolyl)silyl group, a dimethylphenylsilyl group and the like.

The thio group includes a thio group bonded to an alkyl group having 1 to 4 carbon atoms such as a methylthio group, an ethylthio group and an isopropylthio group; and a thio group bonded to an aryl group having 6 to 14 carbon atoms that may have a substituent such as a phenylthio group. The substituent that the aryl group has includes an alkyl group having 1 to 4 carbon atoms, an alkoxy group having 1 to 4 carbon atoms and the like.

The polymer chain includes a 6,6-nylon chain, a vinyl polymer chain, a styrene polymer chain and the like.

When $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$ and $R^{2'}$ and $R^{1'}$ are taken together to form a ring, the ring structure including an aryl group of the general formula (2) and the general formula (2') includes a naphthalene ring, an anthracene ring, a quinoline ring, a phenanthrene ring, a 1,3-benzodioxol ring, a benzothiophene ring, a benzoquinoline ring, a benzo-1,4-dioxolane ring, a benzooxazoline ring, a dihydrobenzooxazoline ring, a benzofuran ring, a benzofurazan ring, a benzo-1,4-dithiorane ring, a benzoimidazoline ring, an azulene ring and the like.

In a diol compound represented by the general formula (3-A) or the general formula (3-B) and a ligand derived from each of them and represented by the general formula (3-A') or the general formula (3-B'), $R^5$, $R^6$, $R^7$ and $R^8$ each independently represent an aryl group that may have a substituent, a heterocyclic group that may have a substituent, an aliphatic chain that may have a substituent or an alicyclic group that may have a substituent. $R^5$ and $R^6$ or $R^7$ and $R^8$ may be taken together to form a ring.

In the general formula (3-A) and the general formula (3-A'), ring A is a 3- to 8-membered ring that may have a hetero element.

In the general formula (3-B) or the general formula (3-B'), $Y^1$ and $Y^2$ each independently represent an aliphatic chain that may have a substituent, an alicyclic group that may have a substituent, an aryl group that may have a substituent, a heterocyclic group that may have a substituent, an alkoxy group, a siloxy group that may have a substituent or a carboxy group.

In the general formula (1') where n=1, a diol compound represented by the general formula (3-A) or the general formula (3-B) and a ligand derived from each of them and represented by the general formula (3-A') or the general formula (3-B') are optically active substances. The optically active substances are represented by the following formulas, respectively. Symbol * means an asymmetric carbon atom.

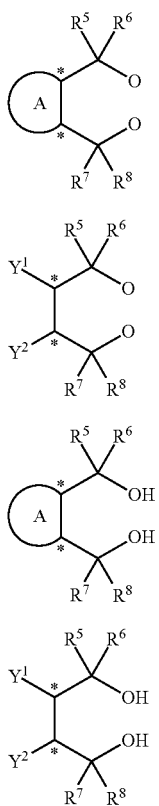

(3-A')

(3-B')

(3-A)

(3-B)

In the general formula (1') where n=2, a diol compound represented by the general formula (3-A) or the general formula (3-B) and a ligand derived from each of them and represented by the general formula (3-A') or the general formula (3-B') may not be necessarily optically active substances.

In a diol compound represented by the general formula (3-A) or the general formula (3-B) and a ligand represented by the general formula (3-A') or the general formula (3-B'), specific examples of the groups represented by $R^5, R^6, R^7$ and $R^8$ will be described.

The aryl group that may have a substituent includes an aryl group having 6 to 14 carbon atoms, preferably 6 to 10 carbon atoms. Specific examples thereof include a phenyl group, a naphthyl group, an anthranyl group, a phenanthryl group and the like. The substituent that the aryl group may have includes an alkyl group having 1 to 4 carbon atoms, an alkoxy group having 1 to 4 carbon atoms and the like, as well as polymer chains such as a 6,6-nylon chain, a vinyl polymer chain, and a styrene polymer chain.

The heterocyclic group that may have a substituent includes an aliphatic heterocyclic group having 2 to 14 carbon atoms such as a piperidino group, a piperazinyl group, a morpholino group, a tetrahydrofuryl group, a tetrahydropyranyl group and a tetrahydrothienyl group; an aromatic heterocyclic group having 4 to 14 carbon atoms such as a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphthyridyl group, a chinolyl group, a benzoimidazolyl group, a benzooxazolyl group and a benzothiazolyl group; and the like. The substituent that the heterocyclic group has includes an alkyl group having 1 to 4 carbon atoms, an alkoxy group having 1 to 4 carbon atoms and the like, as well as polymer chains such as a 6,6-nylon chain, a vinyl polymer chain, and a styrene polymer chain.

The aliphatic chain that may have a substituent includes a linear or branched alkyl group having 1 to 8 carbon atoms, preferably 1 to 4 carbon atoms. Specific examples thereof include a methyl group, an ethyl group, a propyl group, an isopropyl group, a n-butyl group, a sec-butyl group, an isobutyl group and a tert-butyl group. The substituent that the aliphatic chain has includes an alkyl group having 1 to 4 carbon atoms, an alkoxy group having 1 to 4 carbon atoms and the like, as well as polymer chains such as a 6,6-nylon chain, a vinyl polymer chain, and a styrene polymer chain.

The alicyclic group that may have a substituent includes an alicyclic group having 3 to 14 carbon atoms, preferably 3 to 8 carbon atoms. Specific examples thereof include a cyclopropyl group, a cyclobutyl group, a cyclopentyl group, a cyclohexyl group, a cycloheptyl group, a cyclooctyl group and the like. The substituent that the alicyclic group has includes an alkyl group having 1 to 4 carbon atoms, an alkoxy group having 1 to 4 carbon atoms and the like, as well as polymer chains such as a 6,6-nylon chain, a vinyl polymer chain, and a styrene polymer chain.

The hetero element in ring A of each of the general formula (3-A) and the general formula (3-A') includes sulfur, oxygen, nitrogen, boron, silicon, other metal elements capable of forming a metallacycle and the like. A plurality of hetero elements may be present in ring A. In this case, the hetero elements may be the same or different.

Ring A may have a substituent and the hetero element may have a substituent.

Specific examples of the ring A include a benzene ring, a cyclopropane ring, a cyclobutane ring, a cyclopentane ring, a cyclohexane ring, a cycloheptane ring, a cyclooctane ring, a cyclohexene ring, a norbornane ring, a norbornene ring, a tetrahydrofuran ring, a dioxolane ring, a dioxane ring, a dioxacycloheptane ring, a trioxacycloheptane ring, a lactone ring, a lactam ring, a morpholine ring, a pyrrolidine ring, a piperidine ring, a tetrahydrothiophene ring and the like.

Furthermore, the substituents that these ring structures can have include an alkyl group having 1 to 8 carbon atoms, an aryl group having 6 to 14 carbon atoms, an aralkyl group having 7 to 15 carbon atoms, an alkoxy group having 1 to 8 carbon atoms, a vinyl polymer chain, a styrene polymer chain and the like.

The diol compounds represented by the general formula (3-A) and the general formula (3-A') may each form a polymer chain via the substituent or a carbon chain that ring A has.

Specific examples of the groups represented by $Y^1$ and $Y^2$ of the general formula (3-B) or the general formula (3-B') will be described.

The aliphatic chain that may have a substituent, the alicyclic group that may have a substituent, the aryl group that may have a substituent and the heterocyclic group that may have a substituent includes the same examples as those mentioned for $R^1, R^2, R^3, R^4, R^{1'}, R^{2'}, R^{3'}, R^{4'}, R^5, R^6, R^7$ and $R^8$ above.

The alkoxy group includes besides an aliphatic alkoxy group, an aryloxy group, an aralkyloxy group and the like. The aliphatic alkoxy group includes a linear or branched alkoxy group having 1 to 8 carbon atoms, which may have a ring structure. Specific examples thereof include a methoxy group, an ethoxy group, a propoxy group, an isopropoxy group, a n-butoxy group, a sec-butoxy group, an isobutoxy group, a tert-butoxy group, a cyclohexyl group and a n-octyl group. The aryloxy group includes a phenoxy group, a naphthoxy group and the like. The aralkyloxy group includes a benzyloxy group, a 1-phenethyloxy group and the like.

The siloxy group that may have a substituent includes a siloxy group having a hydrocarbon substituent having 1 to 12 carbon atoms. Specific examples thereof include a trimethylsiloxy group, a triethylsiloxy group, a triisopropylsiloxy group, a triphenylsiloxy group, a dimethyl-tert-butylsiloxy group, a diethylphenylsiloxy group and a diphenyl-tert-butylsiloxy group. The substituent that the siloxy group has includes an alkyl group having 1 to 4 carbon atoms, an alkoxy group having 1 to 4 carbon atoms, a silyl group, a siloxy group and the like, as well as a polymer chains such as a 6,6-nylon chain, a vinyl polymer chain, and a styrene polymer chain.

The carboxy group includes a carboxy group derived from a carboxylic acid, for example, a carboxy group having 2 to 18 carbon atoms. Specific examples thereof include an acetoxy group, a propionyloxy group, an acryloyloxy group, a butyryloxy group, a pivaloyloxy group, a pentanoyloxy group, a hexanoyloxy group, a lauroyloxy group, a stearoyloxy group and a benzoyloxy group.

Specific examples of the biaryl diol compound represented by the general formula (2) of the present invention preferably include, but are not limited to, the following compounds.

In the following compounds, Ph represents a phenyl group; Me represents a methyl group. The same shall apply hereinafter.

Symbol * represents a polymer chain bond. Symbol o indicates 1 to 500 and symbol p indicates 1 to 500.

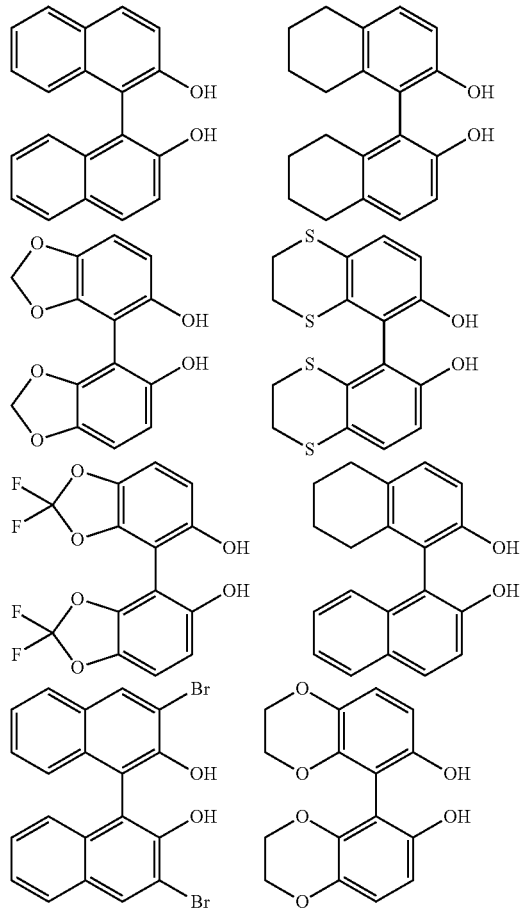

-continued

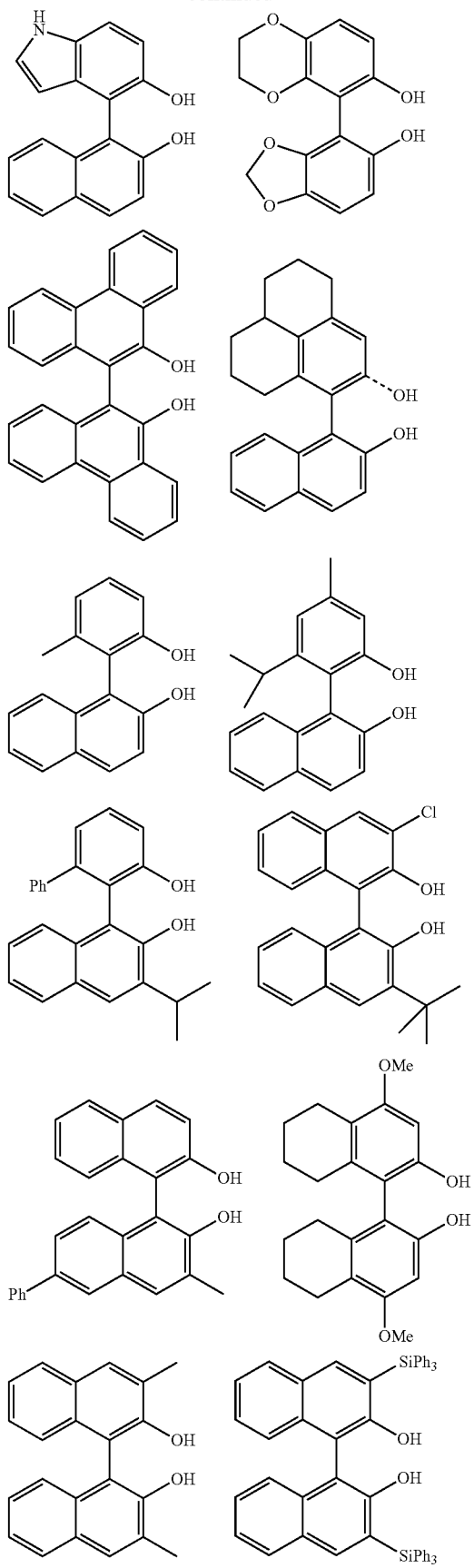

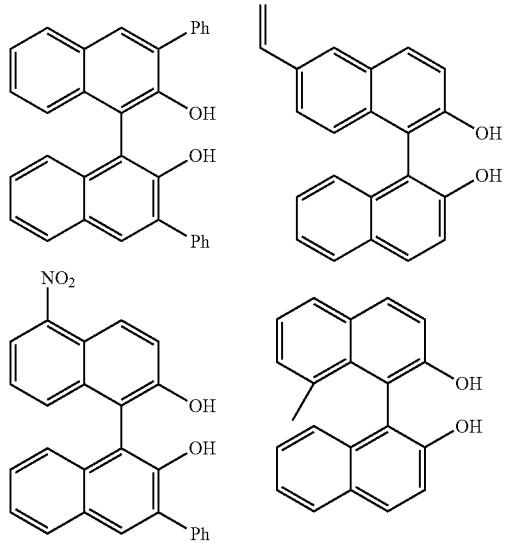
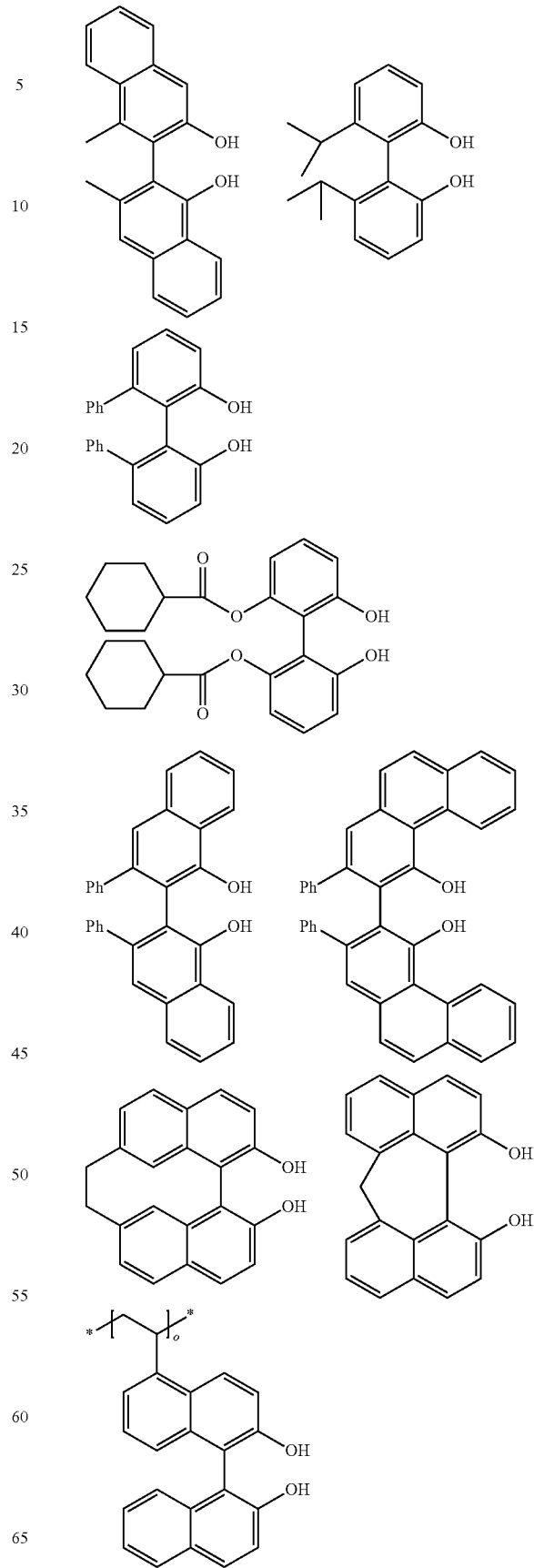

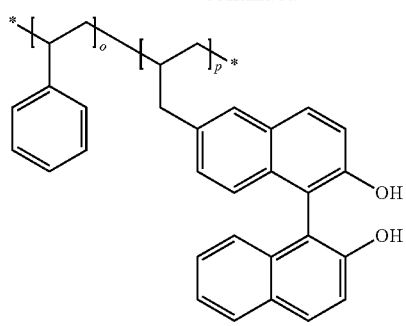

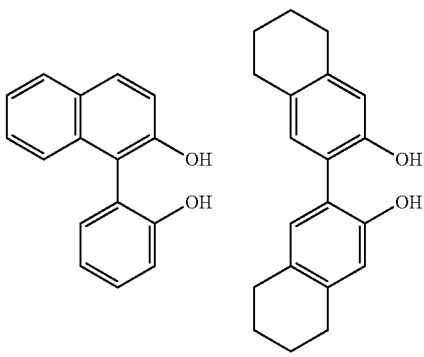

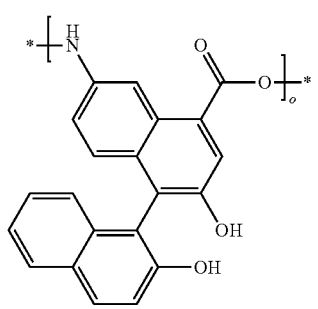

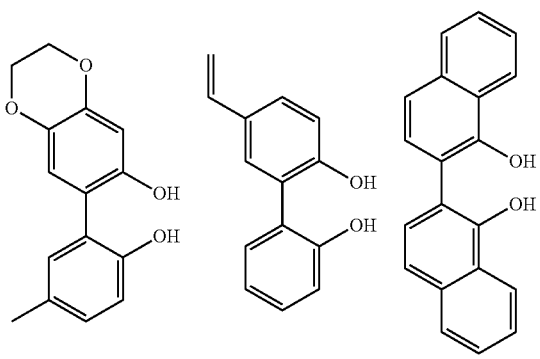

In the general formula (1') where n=1, specific examples of the biaryl diol compound used for synthesis of an aluminum complex and represented by the general formula (2) preferably include, but are not limited to, the following compounds in addition to the aforementioned compounds.

In the compounds, Symbol * represents a polymer chain bond. Symbol o indicates 1 to 500 and symbol p indicates 1 to 500.

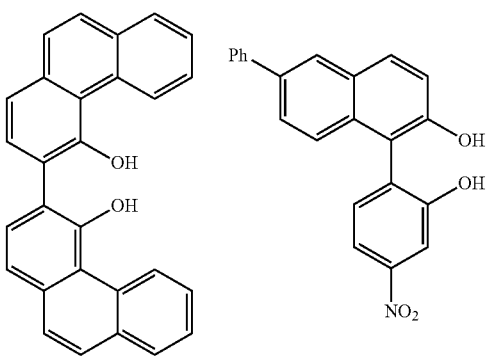

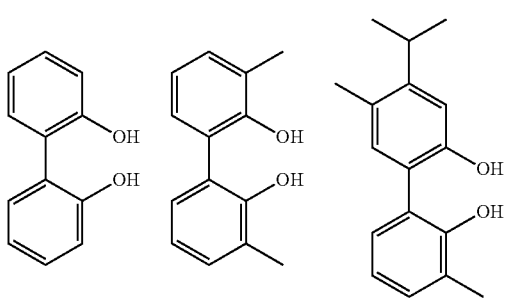

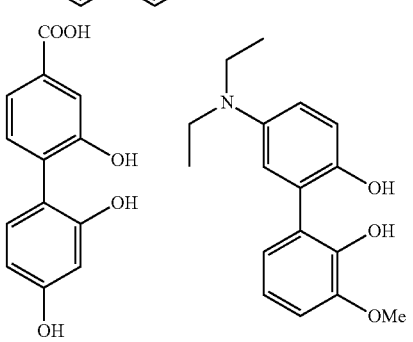

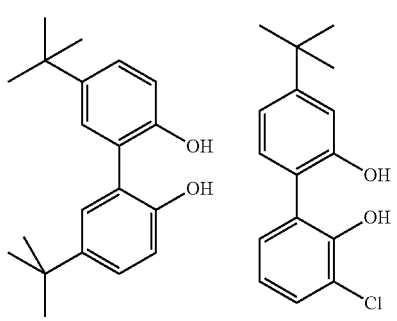

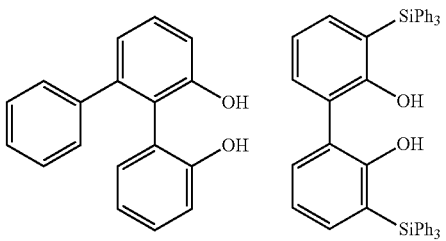

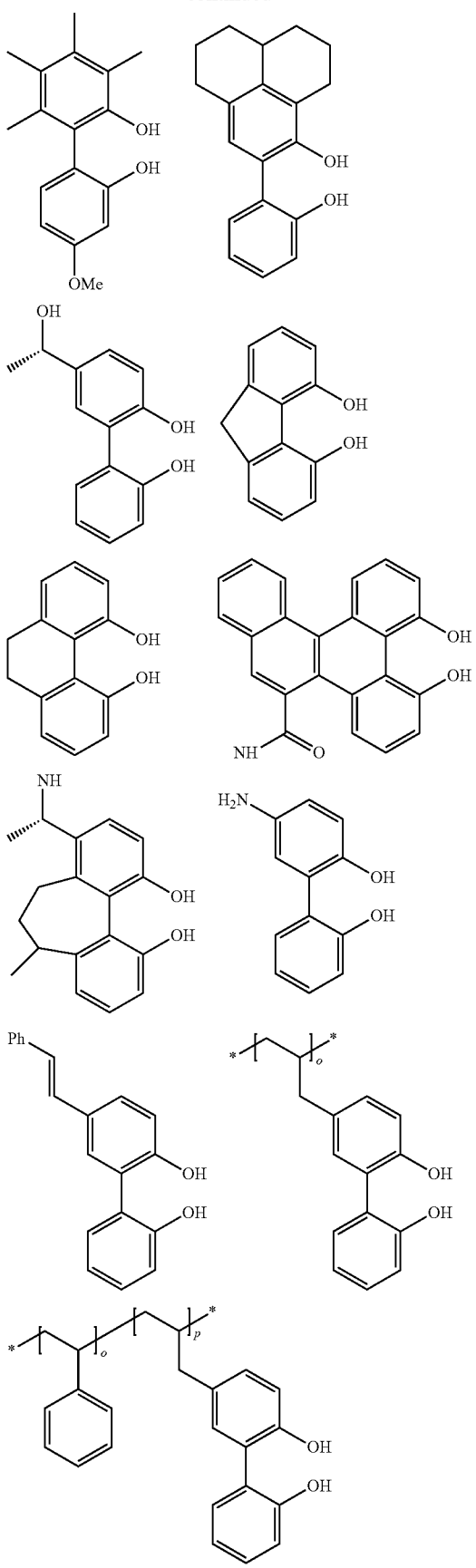

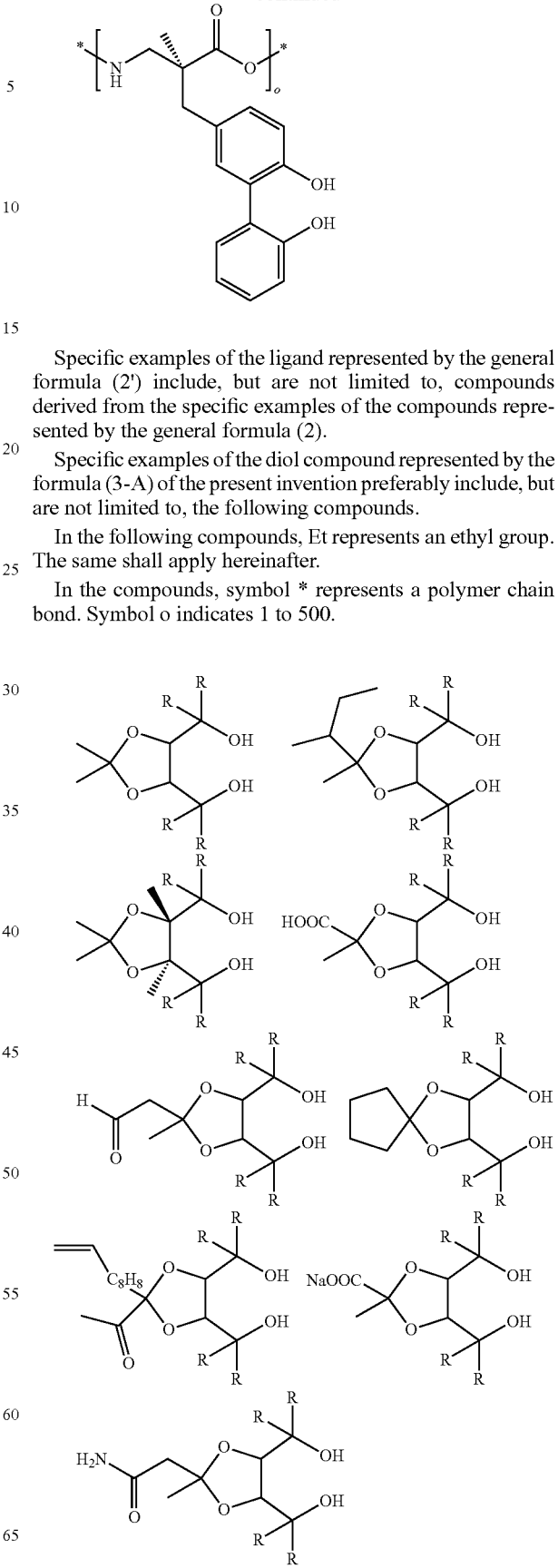

Specific examples of the ligand represented by the general formula (2') include, but are not limited to, compounds derived from the specific examples of the compounds represented by the general formula (2).

Specific examples of the diol compound represented by the formula (3-A) of the present invention preferably include, but are not limited to, the following compounds.

In the following compounds, Et represents an ethyl group. The same shall apply hereinafter.

In the compounds, symbol * represents a polymer chain bond. Symbol o indicates 1 to 500.

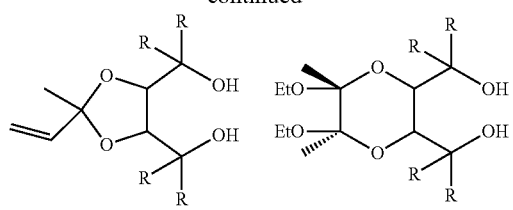
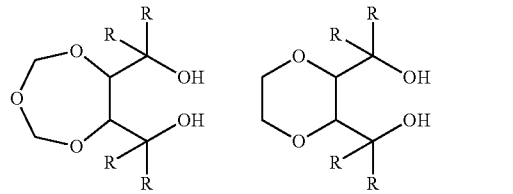
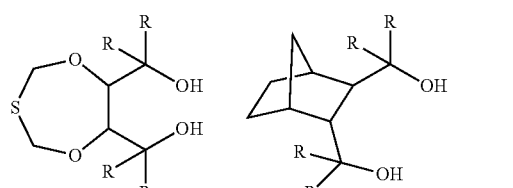
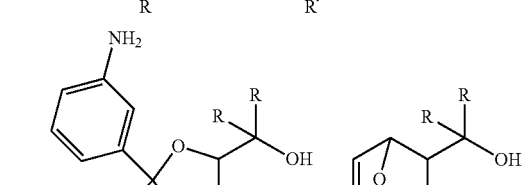
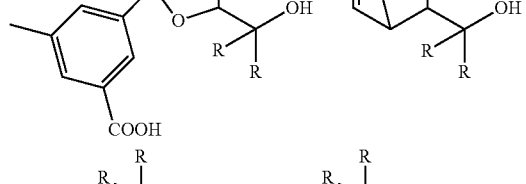
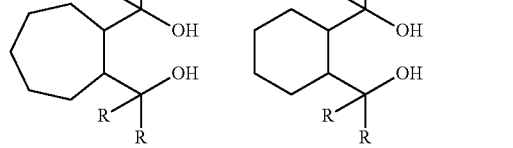
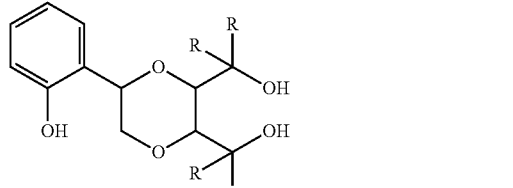
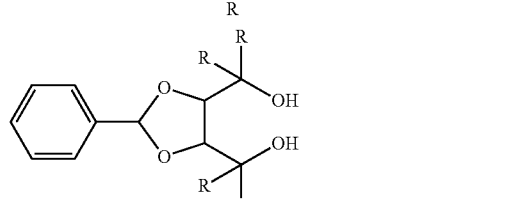
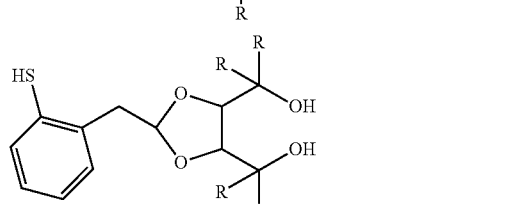
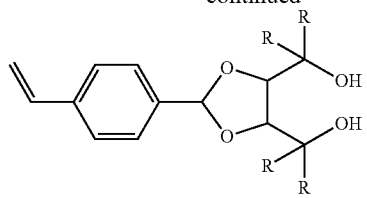
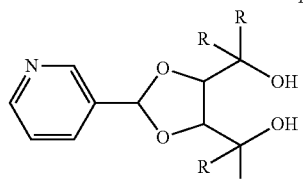
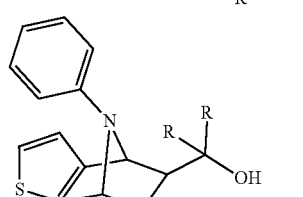
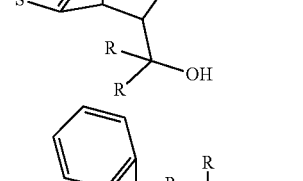
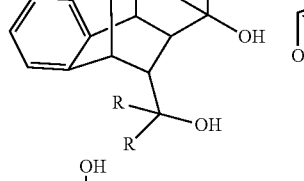
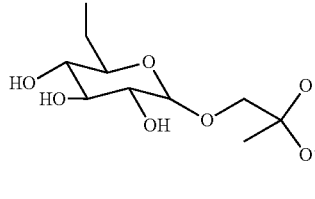
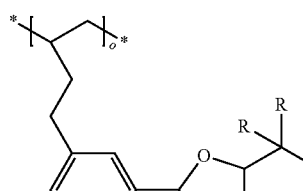
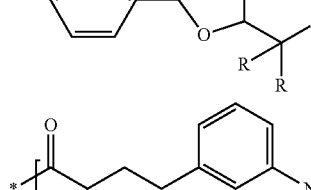
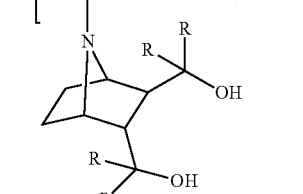

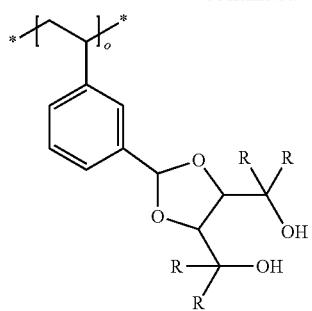

In the aforementioned compounds, R represents a substituent. Specific examples of R are shown below. The four substituents represented by R in the above compounds may be the same or different. Two or three of the four substituents may be the same.

In the substituents R shown below, symbol * represents a binding site, and symbol ** represents a polymer chain bond. Symbol o indicates 1 to 500.

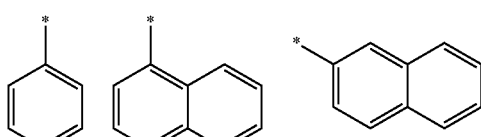
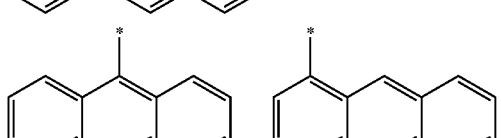
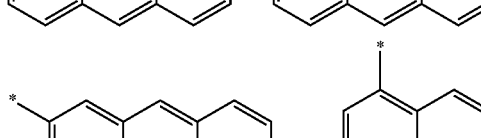
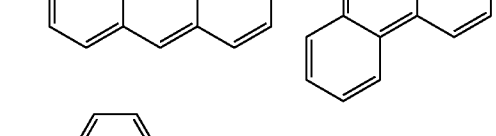
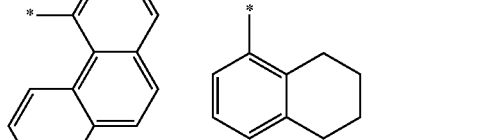
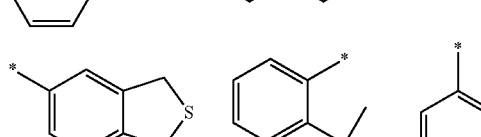
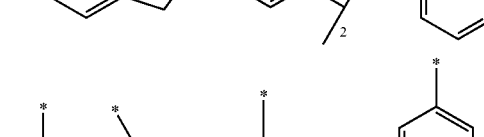
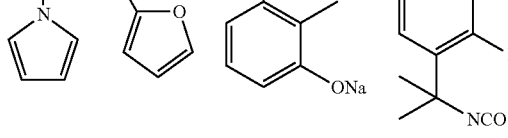

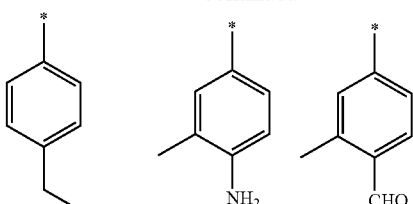
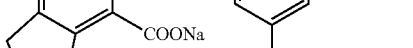
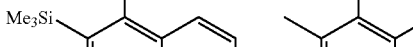
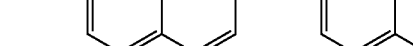
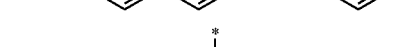
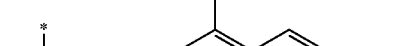
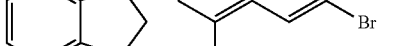

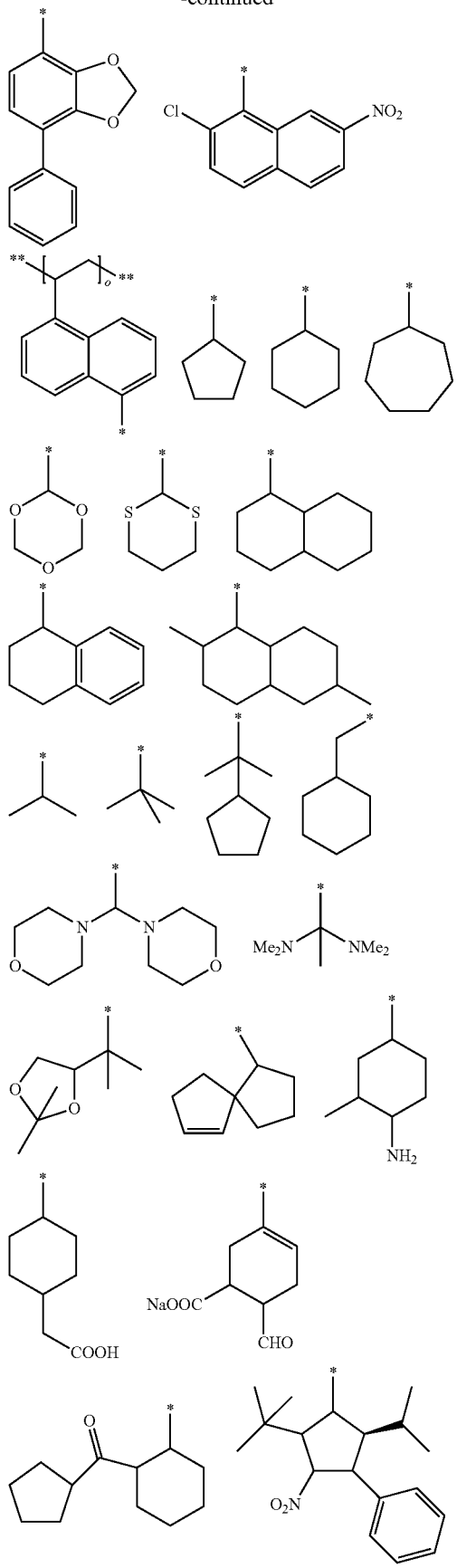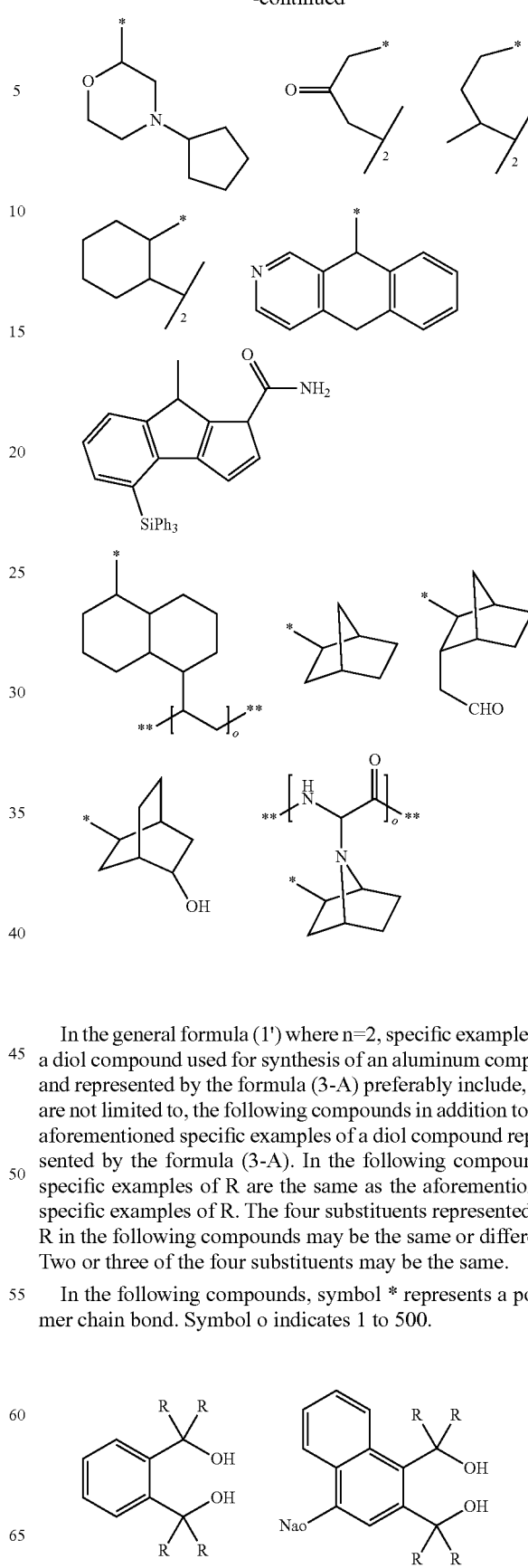

In the general formula (1') where n=2, specific examples of a diol compound used for synthesis of an aluminum complex and represented by the formula (3-A) preferably include, but are not limited to, the following compounds in addition to the aforementioned specific examples of a diol compound represented by the formula (3-A). In the following compounds, specific examples of R are the same as the aforementioned specific examples of R. The four substituents represented by R in the following compounds may be the same or different. Two or three of the four substituents may be the same.

In the following compounds, symbol * represents a polymer chain bond. Symbol o indicates 1 to 500.

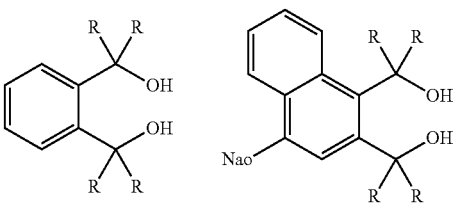

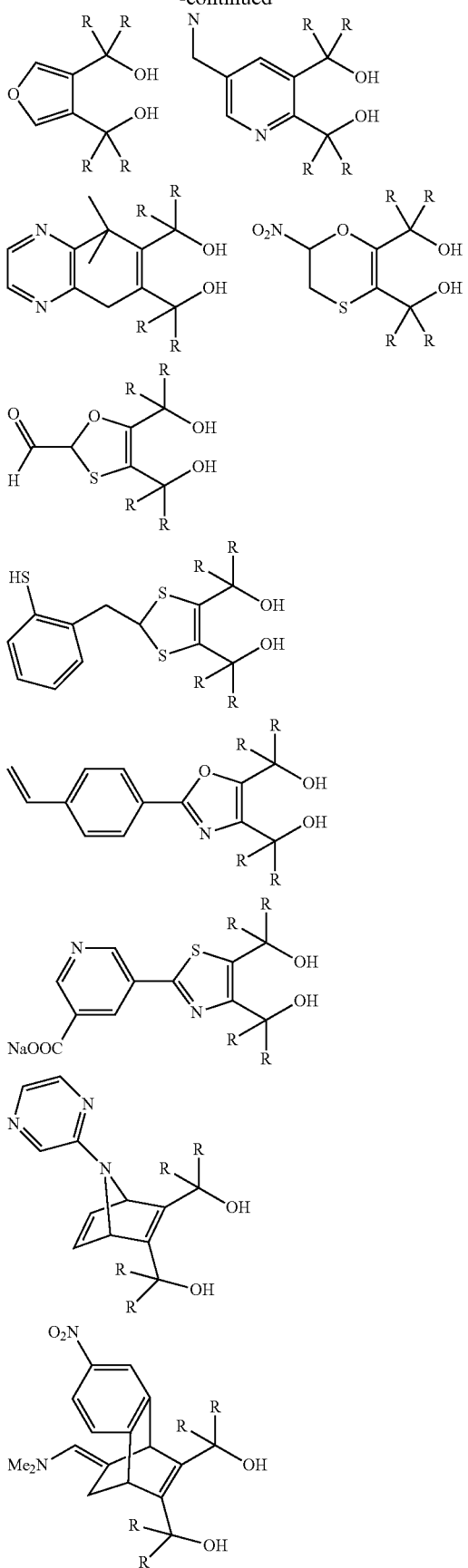
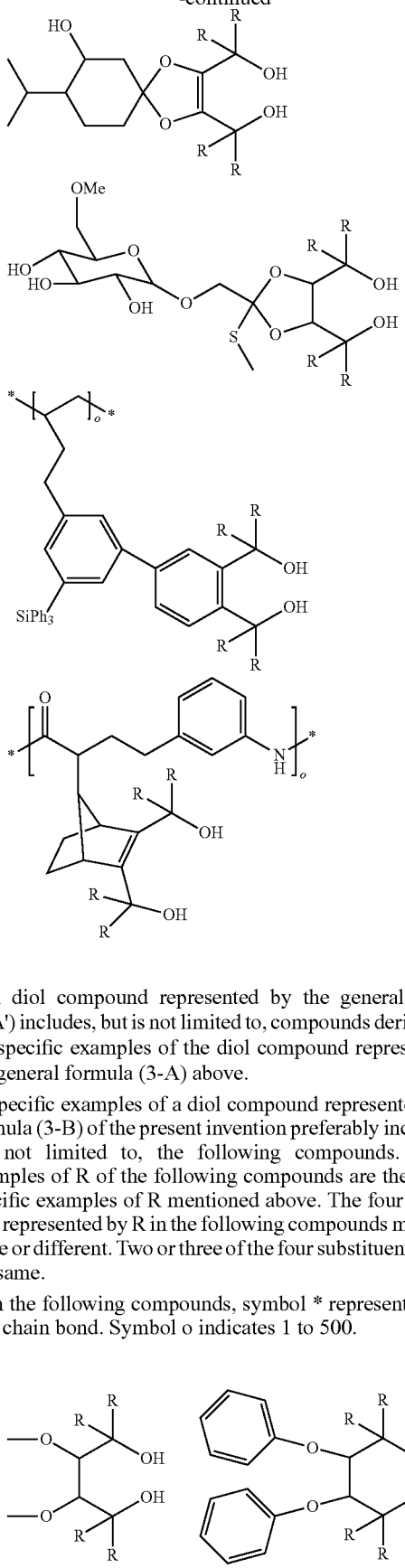

A diol compound represented by the general formula (3-A') includes, but is not limited to, compounds derived from the specific examples of the diol compound represented by the general formula (3-A) above.

Specific examples of a diol compound represented by the formula (3-B) of the present invention preferably include, but are not limited to, the following compounds. Specific examples of R of the following compounds are the same as specific examples of R mentioned above. The four substituents represented by R in the following compounds may be the same or different. Two or three of the four substituents may be the same.

In the following compounds, symbol * represents a polymer chain bond. Symbol o indicates 1 to 500.

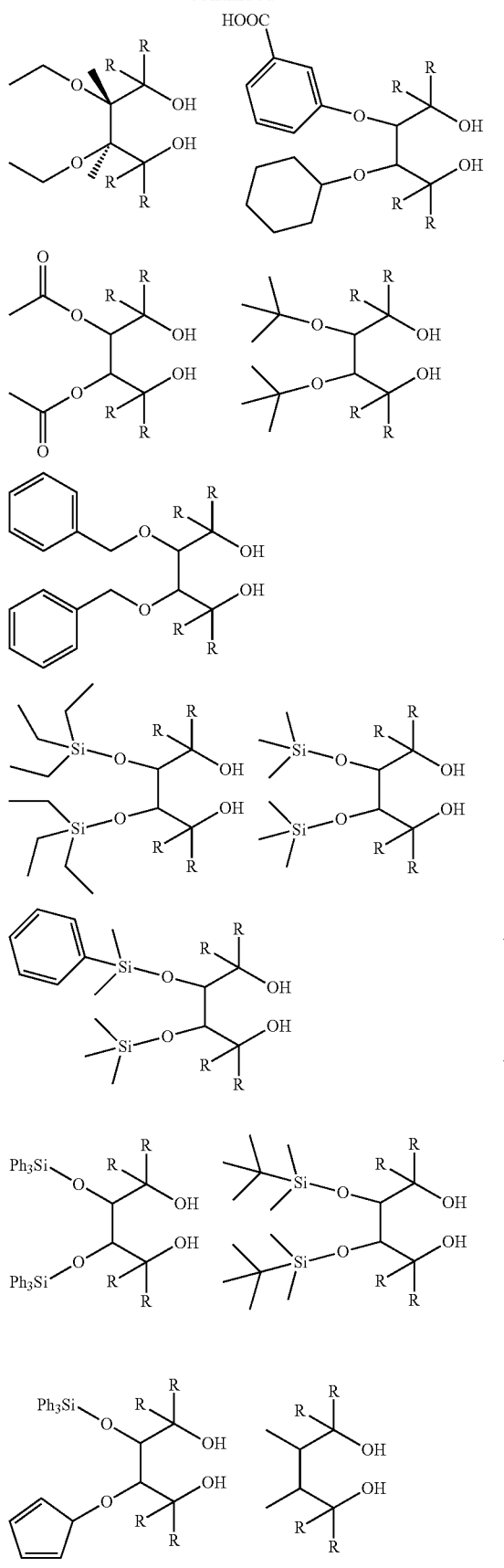
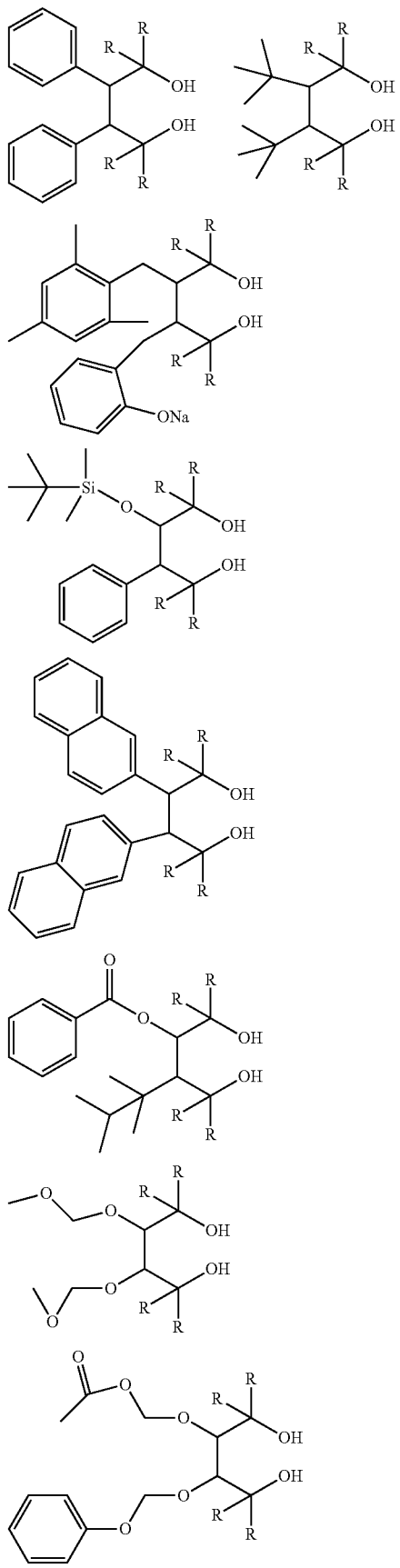

-continued

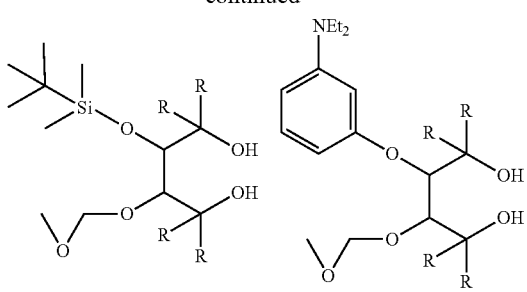
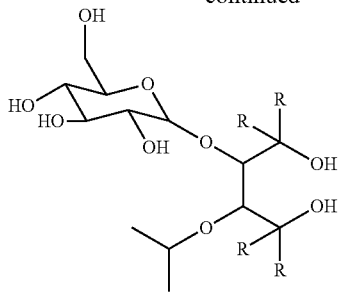
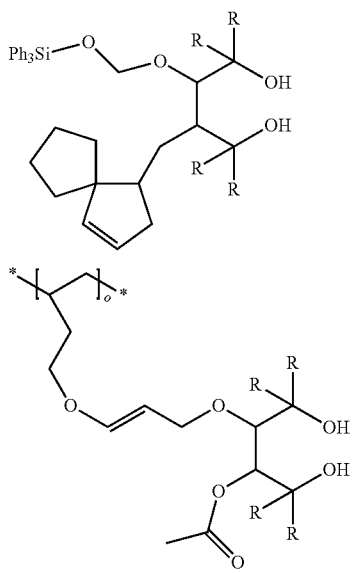
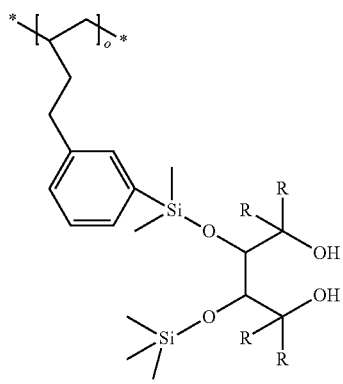
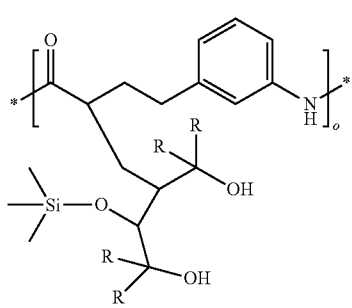

-continued

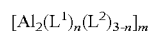

Specific examples of a ligand represented by the general formula (3-B') include, but are not limited to, compounds derived from the aforementioned specific examples of a compound represented by the general formula (3-B).

An aluminum complex represented by the general formula (1') will be described.

$$[Al_2(L^1)_n(L^2)_{3-n}]_m \qquad (1')$$

In the formula (1'), n represents an integer of 1 or 2; m represents a natural number, preferably a natural number of 1 to 10; $L^1$ represents a ligand represented by the general formula (2'); $L^2$ represents a ligand represented by the general formula (3-A') or the general formula (3-B'), with the proviso that when n=2, a ligand represented by the general formula (2') is an optically active substance and when n=1, a ligand represented by the general formula (3-A') or the general formula (3-B') is an optically active substance.

Next, a process for preparing an aluminum complex of the present invention will be described.

The aluminum complex of the present invention is obtained by reacting an aluminum compound represented by the general formula (1), a biaryl diol compound represented by the general formula (2) and a diol compound represented by the general formula (3-A) or the general formula (3-B).

A process for preparing an aluminum complex will be described separately with respect to the cases represented by the formula (1') where n=1 and where n=2.

In the formula (1') where n=1, in an inert organic solvent, e.g., a hydrocarbon (hexane, heptane, benzene, toluene, xylene, etc.), ether (diethyl ether, diisopropyl ether, tetrahydrofuran, etc.) or a halogenated hydrocarbon (dichloromethane, dichloroethane, chlorobenzene, bromotoluene, etc.), an aluminum compound of the general formula (1) is reacted with a diol compound represented by the general formula (3-A) or the general formula (3-B) (about 0.9 to 1.3 fold by mole relative to the aluminum compound) at a temperature of about −30 to 60° C., preferably about −10 to 40° C., more preferably, about 0 to 30° C., for about 0.25 to 30 hours, preferably about 0.5 to 2 hours. Subsequently, a biaryl diol compound of the general formula (2) (about 0.4 to 0.8 fold by mole relative to the aluminum compound) is added and reacted at a temperature of about −30 to 60° C., preferably about −10 to 40° C., more preferably, at about 0 to 30° C., for about 0.25 to 30 hours, preferably about 0.5 to 3 hours. In this manner, an aluminum complex can be easily synthesized.

When a biaryl diol compound of the general formula (2) is added, the biaryl diol compound of the general formula (2) may be directly added to the reaction solution of an aluminum compound of the general formula (1) and a diol compound of the general formula (3-A) or the general formula (3-B). Alternatively, a biaryl diol compound of the general formula (2) may be diluted with a solvent in advance and then added to the reaction solution.

Furthermore, the reaction solution of an aluminum compound of the general formula (1) and a diol compound of the general formula (3-A) or the general formula (3-B) may be added to a biaryl diol compound of the general formula (2).

A biaryl diol compound of the general formula (2) and a diol compound of the general formula (3-A) or the general formula (3-B) cannot be added simultaneously to an aluminum compound of the general formula (1) for reaction. A biaryl diol compound of the general formula (2) must be reacted after an aluminum compound of the general formula (1) and a diol compound of the general formula (3-A) or the general formula (3-B) are reacted.

In the formula (1') where n=2, in an inert organic solvent, e.g., a hydrocarbon (hexane, heptane, benzene, toluene, xylene, etc.), ether (diethyl ether, diisopropyl ether, tetrahydrofuran, etc.) or a halogenated hydrocarbon (dichloromethane, dichloroethane, chlorobenzene, bromotoluene, etc.), an aluminum compound of the general formula (1) is reacted with a biaryl diol compound represented by the general formula (2) (about 0.9 to 1.3 fold by mole relative to the aluminum compound) at a temperature of about −30 to 60° C., preferably about −10 to 40° C., more preferably, about 0 to 30° C. for about 0.25 to 30 hours, preferably about 0.5 to 2 hours. Next, the diol compound of the general formula (3-A) or the general formula (3-B) (about 0.4 to 0.8 fold by mole relative to the aluminum compound) is added and reacted at a temperature of about −30 to 60° C., preferably about −10 to 40° C., more preferably, about 0 to 30° C. for about 0.25 to 30 hours, preferably about 0.5 to 3 hours. In this manner, an aluminum complex can be easily synthesized.

When a diol compound of the general formula (3-A) or the general formula (3-B) is added, the diol compound of the general formula (3-A) or the general formula (3-B) may be added directly to the reaction solution of an aluminum compound of the general formula (1) and a biaryl diol compound of the general formula (2). Alternatively, a diol compound of the general formula (3-A) or the general formula (3-B) is diluted with a solvent in advance and then added to the reaction solution.

Furthermore, the reaction solution of an aluminum compound of the general formula (1) and a biaryl diol compound of the general formula (2) may be added to a diol compound of the general formula (3-A) or the general formula (3-B).

A biaryl diol compound of the general formula (2) and a diol compound of the general formula (3-A) or the general formula (3-B) cannot be simultaneously added to an aluminum compound of the general formula (1) for reaction. A diol compound of the general formula (3-A) or the general formula (3-B) must be reacted after an aluminum compound of the general formula (1) and a biaryl diol compound of the general formula (2) are reacted.

The ring closing reaction of an optical isomer mixture of a compound having both a formyl group and a double bond capable of causing a carbonyl-ene ring closing reaction in the same molecule can be conducted by use of the aluminum complex of the present invention. The aluminum complex of the present invention can conduct a selective ring closing reaction of a specific substrate, thereby increasing the proportion of d-form or l-form of a compound produced by ring closure or increasing the proportion of d-form or l-form of the optical isomer mixture which is not reacted by ring closure.

The compound having both a formyl group and a double bond capable of causing a carbonyl-ene ring closing reaction in the same molecule includes a compound represented by the general formula (4).

The compound produced by ring closure includes a compound represented by the general formula (5).

A compound used in the selective ring closing reaction of the present invention and represented by the general formula (4) and a compound produced by ring closure and represented by the general formula (5) will now be described.

In the compounds represented by the general formula (4) and (5), the alkyl group that may have a substituent and is represented by $R^9$, $R^{10}$, $R^{11}$, $R^{12}$, $R^{13}$, $R^{14}$ and $R^{15}$ includes a linear or branched alkyl group having 1 to 8 carbon atoms, preferably 1 to 4 carbon atoms. Specific examples thereof include a methyl group, an ethyl group, a propyl group, an isopropyl group, a n-butyl group, a sec-butyl group, an isobutyl group and a tert-butyl group. The substituents that these alkyl groups have include an alkoxy group having 1 to 6 carbon atoms such as a methoxy group and an ethoxy group; and an aryl group having 6 to 14 carbon atoms such as a phenyl group, a naphthyl group and a tolyl group.

Furthermore, the protecting group of a hydroxy group that may be protected by a protecting group and represented by $R^{11}$ includes an acyl group having 1 to 8 carbon atoms such as an acetyl group, a benzoyl group and a methoxycarbonyl group; an aralkyl group having 7 to 15 carbon atoms such as a benzyl group; and a substituted silyl group having 3 to 30 carbon atoms such as a trimethylsilyl group and a t-butyldimethylsilyl group; and the like.

An example of the compound represented by the general formula (4) includes citronellal, 2,6-dimethyl-5-heptanal, 2,6,10-trimethyl-5,9-undecadienal, 3,7-dimethyl-2-methylene-6-octenal, 3,7,11-trimethyl-6,10-dodecadienal and the like, preferably an optically active citronellal, and more preferably l-citronellal.

An example of the compound represented by the general formula (5) includes isopulegol, 2-(2-propenyl)-5-methylcyclopentanol, 2-(6-methyl-2,5-heptadien-2-yl)-5-methylcyclopentanol, 2-(6-methyl-1,5-heptadien-2-yl)-5-methylcyclopentanol, 2-methylene-3-methyl-6-(2-propenyl)cyclohexanol, 2-(6-methyl-2,5-heptadien-2-yl)-5-methylcyclohexanol, 2-(6-methyl-1,5-heptadien-2-yl)-5-methylcyclohexanol and the like, preferably an optically active isopulegol, and more preferably l-isopulegol.

Next, the selective ring closing reaction will be described.

The selective ring closing reaction for increasing the proportion of an optical isomer according to the present invention will be described below with reference to production of isopulegol by a ring closing reaction of citronellal using an aluminum complex obtained by using 2,2-binaphthol (hereinafter sometimes referred to as BINOL) as a biaryl diol compound of the general formula (2), and 2,2-dimethyl-α,α,α',α'-tetraphenyl-1,3-dioxolane-4,5-dimethanol (hereinafter sometimes referred to as TADDOL) as a diol compound of the general formula (3-A).

The present invention will be comprehensively described with reference to the examples below; however, the present invention is not limited to the substrate and product below.

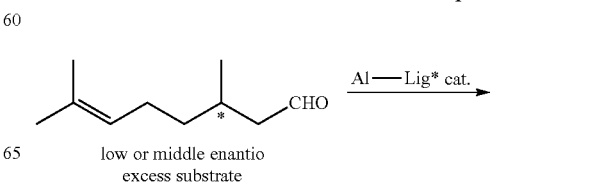

low or middle enantio excess substrate

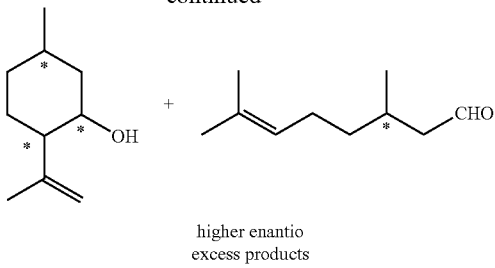

higher enantio
excess products

Al-Lig* cat. in the above represents the aluminum complex of the present invention.

More specifically, citronellal having a low to middle optical purity is subjected to an enantio selective ring closing reaction using the aluminum complex of the present invention as a catalyst to produce isopulegol and citronellal having a higher optical purity than that of citronellal serving as the substrate.

The amount of aluminum catalyst used in the ring closing reaction of the present invention is about 0.05 to 10% by mole in terms of the atomic weight of aluminum (1 mole) relative to a compound represented by the general formula (4), for example, citronellal, preferably about 0.5 to 5% by mole, and further preferably about 0.7 to 2% by mole.

A process for preparing of the aluminum catalyst to be used in the ring closing reaction of the present invention is, for example, as follows:

(A) (a) an aluminum compound of the general formula (1) and a biaryl diol compound of the general formula (2), which is 0.9 to 1.3 fold by mole relative to the aluminum compound, are previously mixed in a reaction system and reacted, further a diol compound of the general formula (3-A) or the general formula (3-B) (0.4 to 0.8 fold by mole relative to the aluminum compound) is mixed and reacted to prepare a catalyst, and thereafter citronellal is added (in-situ process);

(b) an aluminum compound of the general formula (1) and a diol compound of the general formula (3-A) or the general formula (3-B) (0.9 to 1.3 fold by mole relative to the aluminum compound) are mixed and reacted, and further a biaryl diol compound of the general formula (2)(0.4 to 0.8 fold by mole relative to the aluminum compound) is mixed and reacted to prepare a catalyst and thereafter, citronellal is added (in-situ process); or (B) a process of adding the catalyst prepared as mentioned above and citronellal separately at the time of a ring closing reaction.

The same results can be obtained by either process.

The temperature of the ring closing reaction is about −30 to 50° C., preferably about −10 to 30° C., and more preferably about 0 to 20° C. A compound represented by the general formula (5), for example, isopulegol, can be smoothly produced by conducting a reaction, while keeping the above temperature, for about 0.25 to 30 hours and preferably about 0.5 to 20 hours.

The ring closing reaction of the present invention can be conducted in the absence of a solvent or in the presence of an inert solvent.

The solvent to be used is not particularly limited as long as it does not significantly inhibit the reaction. Examples of the solvent include an aliphatic hydrocarbon organic solvent such as hexane, heptane and octane; an alicyclic hydrocarbon organic solvent such as cyclohexane and methylcyclohexane; an aromatic hydrocarbon organic solvent such as benzene, toluene and xylene; a halogenated hydrocarbon organic solvent such as dichloromethane, dichloroethane, chlorobenzene and bromotoluene; an ether organic solvent such as diethyl ether, diisopropyl ether, dimethoxy ethane, tetrahydrofuran, dioxane and dioxolane; and the like. Of these, an organic solvent such as toluene and heptane is more preferably used.

Furthermore, an acid compound and a basic compound may be added at the time of the reaction. Specific examples of the acid compound include hydrochloric acid, sulfuric acid, acetic acid, citronellic acid, geranylic acid, nellic acid, acetic anhydride, propionic anhydride, maleic anhydride, succinic anhydride, pivaloyl acid anhydride and the like. Specific examples of the basic compound include sodium hydroxide, potassium carbonate, triethylamine and the like.

The use amount of these solvents is about 0 to 20 fold relative to the mass of citronellal and preferably 0.5 to 7 fold.

The ring closing reaction is preferably conducted in an inert gas atmosphere such as nitrogen gas or argon gas in order to smoothly conduct the ring closing reaction.

After completion of the ring closing reaction, conventional post treatments such as distillation, crystallization, and various types of chromatographic methods, are performed singly or in combination. In this manner, a reaction product can be purified. For example, to purify isopulegol, a distillation treatment is simply performed without performing cryogenic recrystallization. In this manner, highly purified isopulegol can be obtained. Furthermore, if the residue obtained after the distillation treatment is subjected to a general treatment with acid or alkali to remove aluminum impurities, etc. and then subjected to crystallization, a ligand can be used again.

EXAMPLES

The present invention will be described in detail below with reference to the following non-limiting Examples.

Measurement of reaction products was performed by gas chromatography (GC) in the conditions as described below.

Analysis apparatus used: GC-2010 gas chromatography manufactured by Shimadzu Corporation Column: conversion rate measurement, DB-WAX (0.25 mm×30 m) manufactured by Agilent, Optical purity, beta-DEX-225 (0.25 mm×30 m) manufactured by Supelco, Detector: FID Note that the optical purities of the citronellal isomers used in the present invention are as follows:

d-citronellal: 97.8% e.e.
l-citronellal: 96.6% e.e.
racemic citronellal 0.74% e.e.

Example 1

Preparation of Aluminum Catalyst and Synthesis of L-Isopulegol

Figure 4:
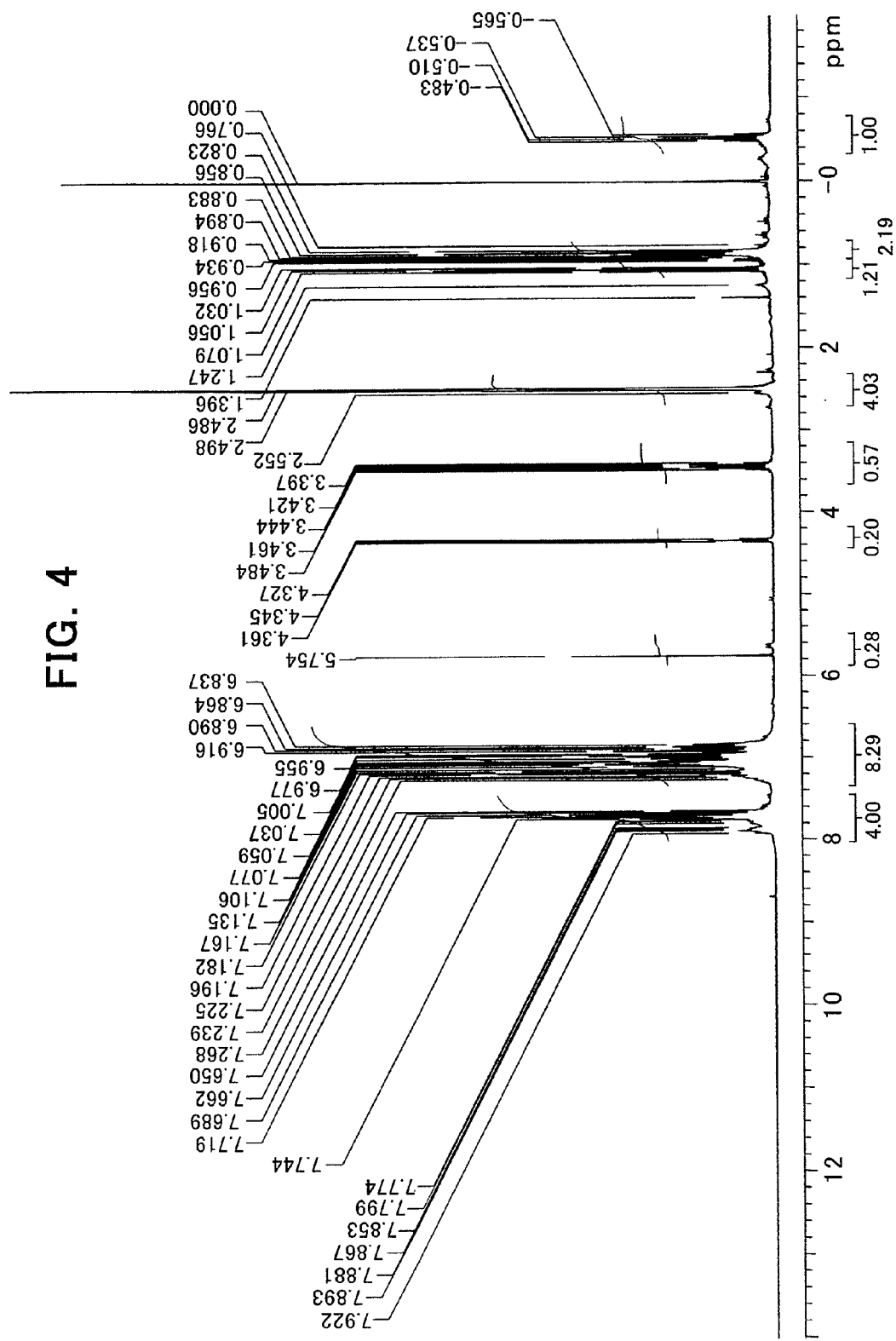
FIG. 4 shows an NMR chart of a solid substance obtained after the reaction of (R)-BINOL and triethylaluminum in Example 1.
Figure 5:
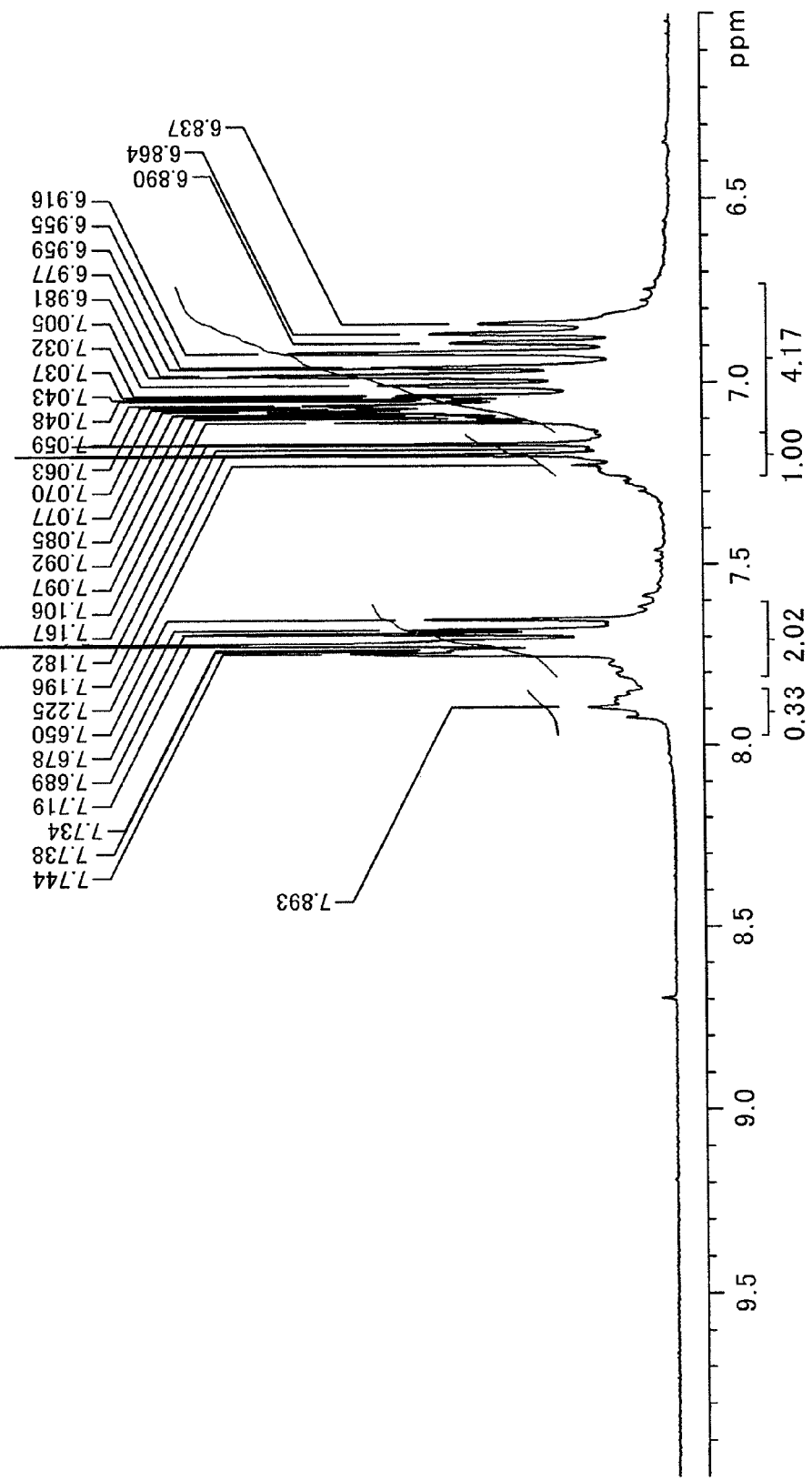
FIG. 5 shows an enlarged chart of a low magnetic field side of the NMR chart shown in FIG. 4.

In a nitrogen atmosphere, 286 mg (1.00 mmol) of (R)-2,2'-dihydroxy-1,1'-binaphthyl (hereinafter sometimes referred to as (R)-BINOL) were placed in a 50-ml reaction flask. After purged with nitrogen, methylene chloride (9 ml) and 1 ml of triethylaluminum-hexane solution (1.00 mmol, 1.0 mol/L) were sequentially added and stirred at room temperature for one hour. At this point, the solvent was distilled away from the reaction system, and the residue was dried under a reduced pressure to obtain a solid substance, which was analyzed by NMR, for reference. The NMR chart is shown in FIG. 4, and an enlarged chart of a low magnetic field side thereof is shown in FIG. 5.

Figure 2:
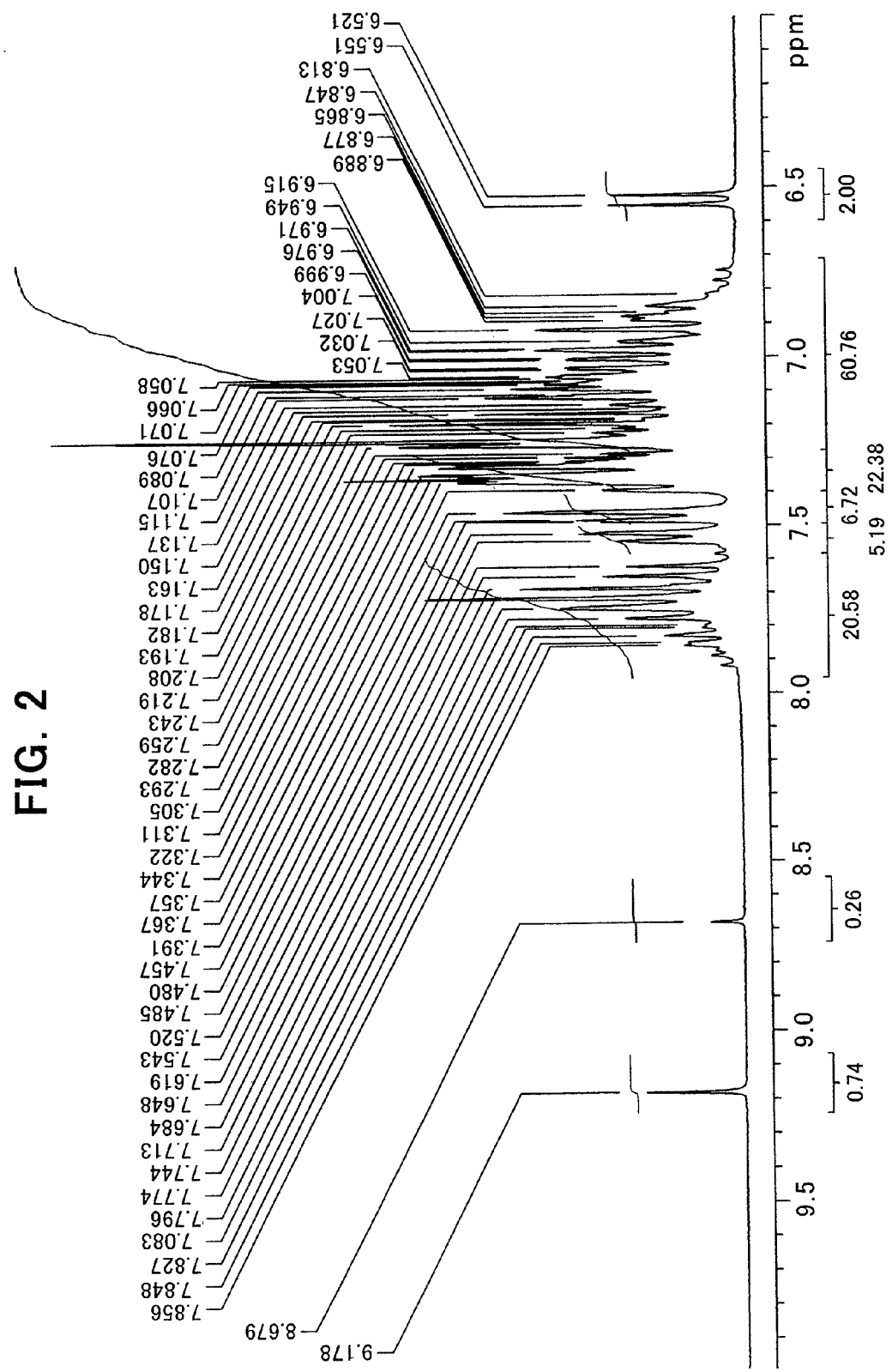
FIG. 2 shows an enlarged chart of a low magnetic field side of the NMR chart shown in FIG. 1.

Furthermore, 233 mg (0.50 mmol) of (R,R)-2,2-dimethyl-α,α,α',α'-tetraphenyl-1,3-dioxolane-4,5-dimethanol (hereinafter sometimes referred to as (R,R)-TADDOL) were added and stirred at room temperature for 3 hours. Thereafter, the solvent was distilled away from the reaction system, and the residue was dried under a reduced pressure. The resultant solid substance was analyzed by NMR. As a result, the peak of an aluminum complex was confirmed in addition to that of a ligand. The NMR chart is shown in FIG. 1 and an enlarged view of a low magnetic field side thereof is shown in FIG. 2.

The solid substance obtained above (300 mg) was added to a solution mixture of d-citronellal (3.08 g, 20 mmol) and methylene chloride (9 ml) cooled to 0 to 5° C. and stirred at 0 to 5° C. for 3 hours. After completion of the reaction, water (2 ml) and toluene (2 ml) were added. The organic layer was analyzed by gas chromatography. As a result, it was found that the substrate conversion rate was 96.9%, the isopulegol selectivity was 99.0%, and the ratio of l-isopulegol to the other isomer was 96.9:3.1.

Figure 3:
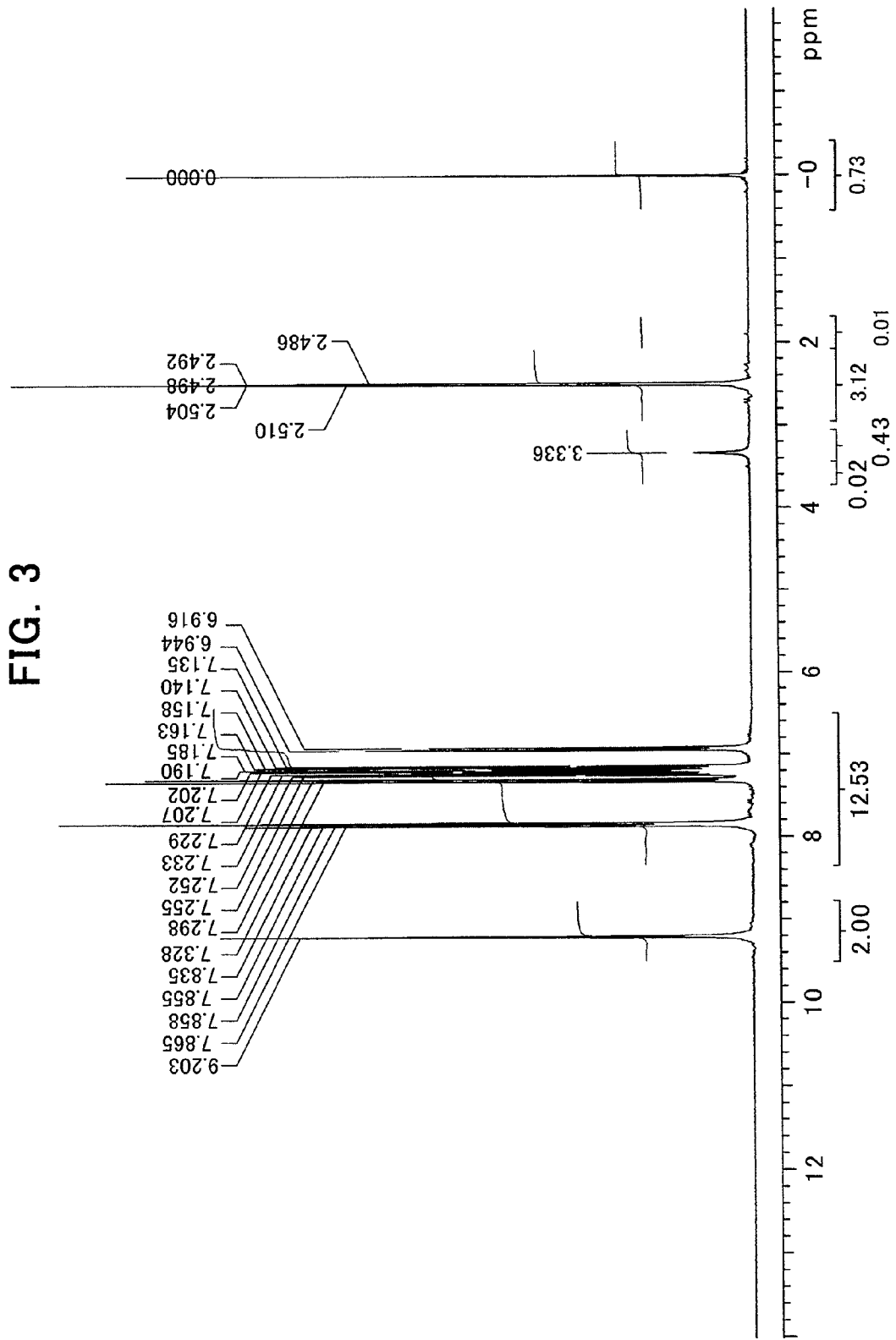
FIG. 3 shows an NMR chart of (R)-BINOL.
Figure 6:
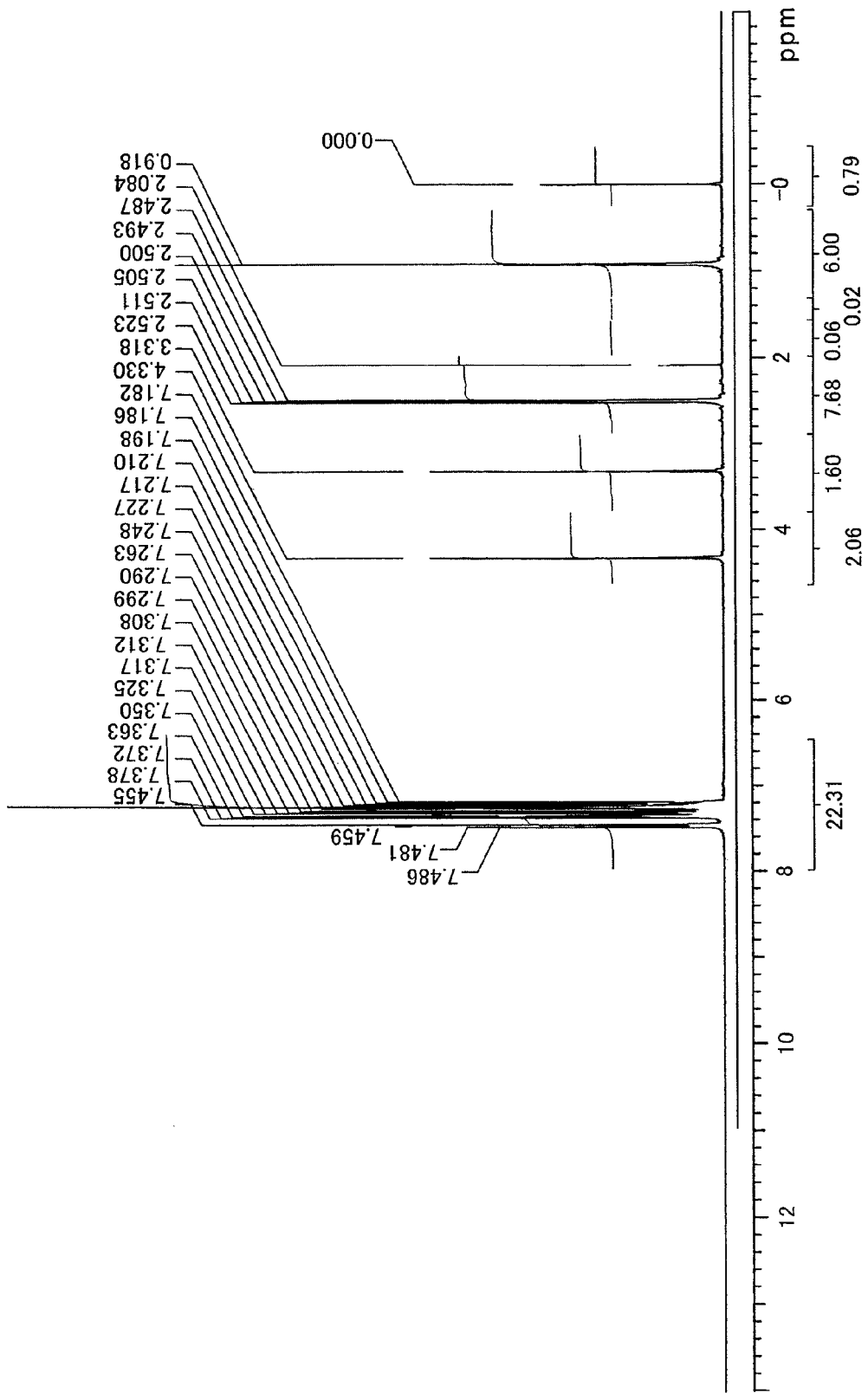
FIG. 6 shows an NMR chart of (R,R)-TADDOL.
Figure 7:
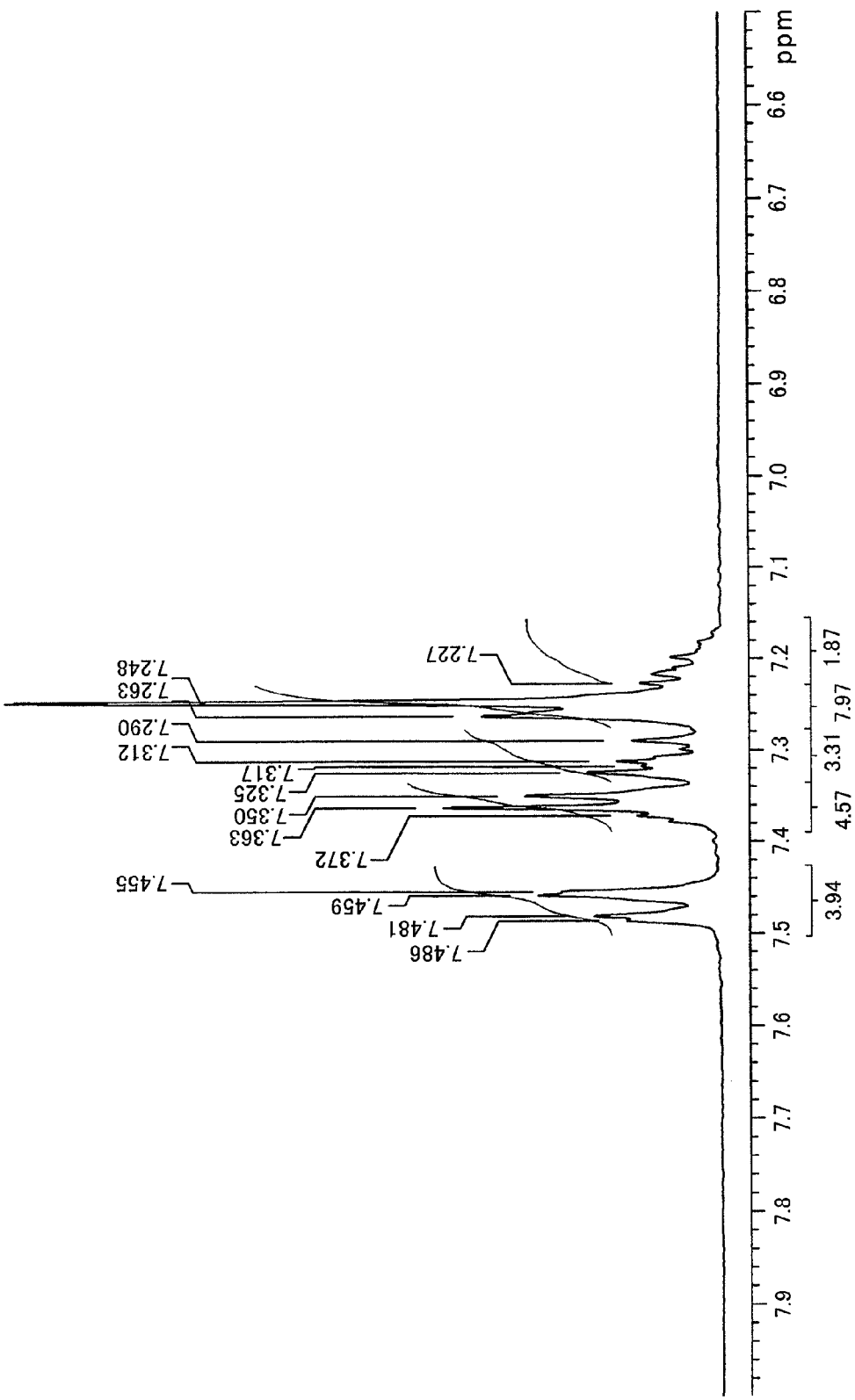
FIG. 7 shows an enlarged chart of a low magnetic field side of the NMR chart shown in FIG. 6.

As a reference, the NMR chart of (R)-BINOL is shown in FIG. 3, the NMR chart of (R,R)-TADDOL is shown in FIG. 6. The enlarged NMR chart of a low magnetic field side of the NMR chart of FIG. 6 is shown in FIG. 7.

Example 2

Synthesis of L-Isopulegol from Racemic Citronellal 143 mg (0.5 mmol) of (R)-2,2'-dihydroxy-1,1'-binaphthyl were placed in a 50 ml-Schlenk tube. After purged with nitrogen, methylene chloride (11.6 ml) and 0.5 ml (0.5 mmol, 1.0 mol/L) of a triethylaluminum-toluene solution were sequentially added and stirred at room temperature for one hour. Furthermore, (R,R)-TADDOL (187 mg, 0.4 mmol) was added and stirred at room temperature for one hour to obtain a catalyst solution. After the catalyst solution was cooled to 0 to 5° C., racemic citronellal (3.86 g, 25 mmol) was added dropwise and stirred at 0 to 5° C. for 5 hours. After completion of the reaction, water (2 ml) was added and the organic layer was analyzed by gas chromatography. As a result, it was found that the substrate conversion rate was 55.2%, the isopulegol selectivity was 87.2%, the enantio selectivity of l-citronellal was 42.8% e.e., and the enantio selectivity of l-n-isopulegol was 58.6% e.e.

The aluminum complex of the present invention using (R)-2,2'-dihydroxy-1,1'-binaphthyl (one-fold by mole relative to aluminum) and (R,R)-TADDOL (0.8 fold by mole) as a ligand had an excellent selectivity of ring-closing d-citronellal of a racemic citronellal to produce l-n-isopulegol.

Examples 3 to 8

Synthesis of Isopulegol by Aluminum Catalyst

Synthesis of isopulegol was performed using various diol compounds or biaryl diol compounds.

A biaryl diol compound of the general formula (2) was added as Lig1 in a 50 ml-Schlenk tube, in Examples 3 to 7 in the amounts listed in Table 1, and a diol compound of the general formula (3-A) was added as Lig1 in Example 8 in the amounts listed in Table 1. After purged with nitrogen, a solvent (3 ml) and triethylaluminum (0.32 mmol) were sequentially added and stirred at room temperature for one hour. Furthermore, a diol compound of the general formula (3-A) was added as Lig2 in Examples 3 to 7 in the amounts listed in Table 1 and a biaryl diol compound of the general formula (2) was added as Lig2 in Example 8 in the amounts listed in Table 1, and stirred at room temperature for one hour to obtain catalyst solutions. After each of the catalyst solutions was cooled to 0 to 5° C., citronellal (1.00 g, 6.48 mmol) was added dropwise and stirred at 0 to 5° C. for one hour. After completion of the reaction, water (2 ml) was added and the organic layer was analyzed by gas chromatography.

The results are shown in Table 1.

In the table, conv. represents the conversion rate of citronellal, sel. represents the selectivity of isopulegol, and n-sel. represents the selectivity of n-isopulegol.

(R)-BINOL, (S)-BINOL, (R,R)-TADDOL, (S,S)-NAPH-TADDOL, NAPH-TADDOL respectively represent the following compounds.

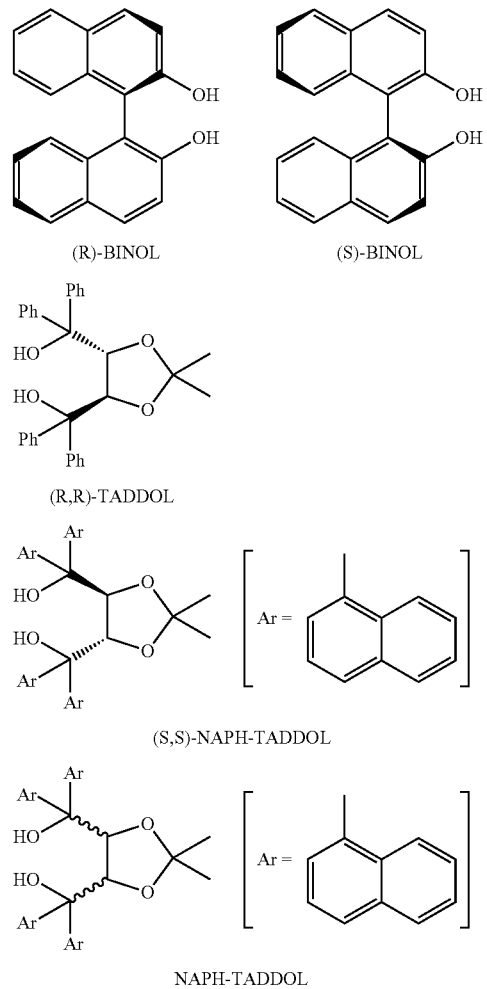

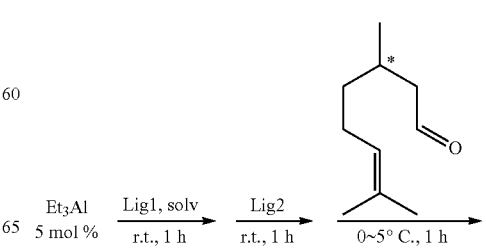

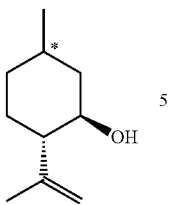
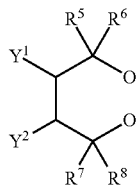

(3-B')

h represents hour.
solv represents a solvent.

in the formula (2'), $R^1$, $R^2$, $R^3$, $R^4$, $R^{1'}$, $R^{2'}$, $R^{3'}$, and $R^{4'}$ each independently represent a hydrogen atom, a halogen

TABLE 1

| Example | Solvent | Citronellal | Lig1 (fold by mole relative to $Et_3Al$) | Lig2 (fold by mole relative to $Et_3Al$) | Conv. (%) | Sel. (%) | n-sel. (%) | n-isopulegol produced |
|---|---|---|---|---|---|---|---|---|
| 3 | $CH_2Cl_2$ | d | (R)-BINOL (1) | (R,R)-TADDOL (0.8) | 81.0 | 99.7 | 96.9 | l |
| 4 | $CH_2Cl_2$ | l | (R)-BINOL (1) | (R,R)-TADDOL (0.8) | 79.4 | 24.9 | 64.6 | d |
| 5 | $CH_2Cl_2$ | d | (S)-BINOL (1) | (S,S)-NAPH-TADDOL (0.8) | 15.4 | 100 | 75.9 | l |
| 6 | $CH_2Cl_2$ | l | (S)-BINOL (1) | (R,R)-TADDOL (0.8) | 53.2 | 95.8 | 94.5 | d |
| 7 | $CH_2Cl_2$ | l | (R)-BINOL (1) | NAPH-TADDOL (0.6) | 77.2 | 98.1 | 95.1 | d |
| 8 | Toluene | d | (S,S)-NAPH-TADDOL (1) | (S)-BINOL (0.8) | 98.7 | 96.8 | 92.9 | l |

The invention claimed is:

1. An aluminum complex represented by the general formula (1') below:

$$[Al_2(L^1)_n(L^2)_{3-n}]_m \quad (1')$$

wherein in the formula (1'), n represents an integer of 1 or 2; m represents a natural number; $L^1$ represents a ligand represented by the formula (2') below; $L^2$ represents a ligand represented by the formula (3-A') below or the formula (3-B') below, with the proviso that when n=2, the ligand represented by the formula (2') below is an optically active substance and when n=1, the ligand represented by the formula (3-A') below or the formula (3-B') below is an optically active substance,

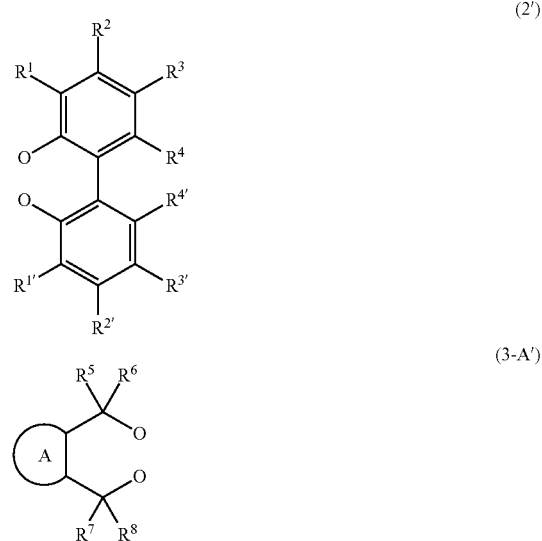

atom, a hydroxy group, a saturated or unsaturated carbon chain, an aryl group that may have a substituent, a heterocyclic group that may have a substituent, an alkoxy group, an aryloxy group, an aralkyloxy group, a carboxy group that may be protected with a protecting group, an amino group, a substituted amino group, a nitro group, an acyl group, a substituted silyl group, a thio group, a mercapto group, or a polymer chain, and $R^1$ and $R^2$, $R^2$ and $R^3$, $R^3$ and $R^4$, $R^4$ and $R^{4'}$, $R^{4'}$ and $R^{3'}$, $R^{3'}$ and $R^{2'}$, and $R^{2'}$ and $R^{1'}$ may be taken together to form a ring;

in the formula (3-A'), $R^5$, $R^6$, $R^7$, and $R^8$ each independently represent an aryl group that may have a substituent, a heterocyclic group that may have a substituent, an aliphatic chain that may have a substituent or an alicyclic group that may have a substituent, and ring A represents a 3- to 8-membered ring that may have a hetero element, and $R^5$ and $R^6$, and $R^7$ and $R^8$ may be taken together to form a ring; and in the formula (3-B'), $R^5$, $R^6$, $R^7$ and $R^8$ have the same meanings as defined above, $Y^1$ and $Y^2$ each independently represent an aliphatic chain that may have a substituent, an alicyclic group that may have a substituent, an aryl group that may have a substituent, a heterocyclic group that may have a substituent, an alkoxy group, a siloxy group that may have a substituent or a carboxy group, and $R^5$ and $R^6$, and $R^7$ and $R^8$ may be taken together to form a ring.

2. A process for producing the aluminum complex according to claim 1, said process comprising the step of reacting an aluminum compound represented by the general formula (1) below:

$$Al(Lg)_3 \quad (1)$$

wherein in the formula (1), Lg represents an alkyl group, an alkoxy group or a halogen atom, with a biaryl diol compound represented by the general formula (2) below, and a diol compound represented by the general formula (3-A) below or the general formula (3-B) below:

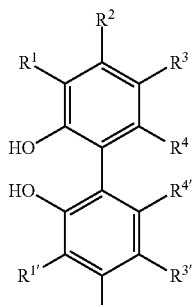

(2)

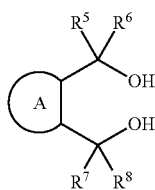

(3-A)

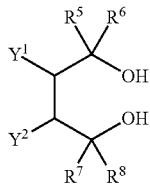

(3-B)

wherein in the formula (2), $R^1$, $R^2$, $R^3$, $R^4$, $R^{1'}$, $R^{2'}$, $R^{3'}$ and $R^{4'}$ have the same meanings as defined in the formula (2') of claim 1;

in the formula (3-A), $R^5$, $R^6$, $R^7$, $R^8$ and ring A have the same meanings as defined in the formula (3-A') of claim 1; and in the formula (3-B), $R^5$, $R^6$, $R^7$, $R^8$, $Y^1$ and $Y^2$ have the same meanings as defined in the formula (3-B') of claim 1.

3. The process for producing the aluminum complex according to claim 2, wherein the biaryl diol compound represented by the general formula (2) is an optically active substance.

4. The process for producing the aluminum complex according to claim 2, wherein the diol compound represented by the general formula (3-A) or the general formula (3-B) is an optically active substance.

5. The process for producing the aluminum complex according to claim 2, wherein the biaryl diol compound represented by the general formula (2) is an optically active substance, and the diol compound represented by the general formula (3-A) or the general formula (3-B) is an optically active substance.

6. A process for producing an optically active compound, said process comprising the step of subjecting an optical isomer mixture of a compound having both a formyl group and a double bond capable of causing a carbonyl-ene ring closing reaction in the same molecule to a ring closing reaction in the presence of the aluminum complex according to claim 1, wherein the optically active compound is enriched with either a d-form or l-form compound produced by the ring closing reaction of the compound having both the formyl group and the double bond.

7. The production process according to claim 6, wherein the compound having both the formyl group and the double bond capable of causing the carbonyl-ene ring closing reaction in the same molecule is a compound represented by the general formula (4) below:

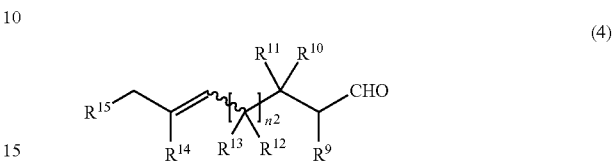

(4)

wherein in the formula (4), n2 represents an integer of 1 or 2; $R^9$, $R^{10}$ and $R^{12}$ each independently represent a hydrogen atom or an alkyl group that may have a substituent; $R^{11}$ represents an alkyl group that may have a substituent or a hydroxy group that may be protected with a protecting group; $R^{13}$, $R^{14}$ and $R^{15}$ each independently represent a hydrogen atom or an alkyl group that may have a substituent; and a wavy line represents an E or Z conformation.

8. The production process according to claim 6, wherein the compound produced by ring closure is a compound represented by the general formula (5) below:

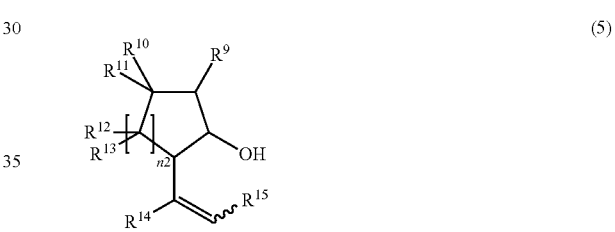

(5)

wherein in the formula (5), n2 represents an integer of 1 or 2; $R^9$, $R^{10}$ and $R^{12}$ each independently represent a hydrogen atom or an alkyl group that may have a substituent; $R^{11}$ represents an alkyl group that may have a substituent or a hydroxy group that may be protected with a protecting group; $R^{13}$, $R^{14}$ and $R^{15}$ each independently represent a hydrogen atom or an alkyl group that may have a substituent; and a wavy line represents an E or Z conformation.

9. The production process according to claim 6, wherein the compound having both the formyl group and the double bond capable of causing the carbonyl-ene ring closing reaction in the same molecule is optically active citronellal and the compound produced by ring closure is optically active isopulegol.

10. The production process according to claim 9, wherein the optically active isopulegol is l-isopulegol.

11. The production process according to claim 9, wherein the optically active citronellal is l-citronellal.

12. A process for enriching either d-form or l-form in an optical isomer mixture of a compound having both a formyl group and a double bond capable of causing a carbonyl-ene ring closing reaction in the same molecule, said process comprising the step of subjecting the optical isomer mixture to a ring closing reaction in the presence of the aluminum complex according to claim 1, wherein either d-form or l-form is not reacted by ring closure.

* * * * *